(12) United States Patent
Miller et al.

(10) Patent No.: US 8,528,589 B2
(45) Date of Patent: Sep. 10, 2013

(54) MANIPULATION OF MICROFLUIDIC DROPLETS

(75) Inventors: Benjamin Miller, Littleton, MA (US);
Brian Hutchison, Medford, MA (US);
Andrew Wilson, Arlington, MA (US);
Jonathan Larson, Chelsea, MA (US);
Qun Zhong, Lexington, MA (US);
Yevgeny Yurkovetsky, Winchester, MA (US); Darren Link, Lexington, MA (US); Mark Weary, North Billerica, MA (US)

(73) Assignee: Raindance Technologies, Inc., Lexington, MA (US)

( * ) Notice: Subject to any disclaimer, the term of this patent is extended or adjusted under 35 U.S.C. 154(b) by 259 days.

(21) Appl. No.: 12/729,462

(22) Filed: Mar. 23, 2010

(65) Prior Publication Data

US 2011/0000560 A1    Jan. 6, 2011

Related U.S. Application Data

(60) Provisional application No. 61/162,521, filed on Mar. 23, 2009.

(51) Int. Cl.
*F16K 31/36* (2006.01)

(52) U.S. Cl.
USPC ............. 137/487.5; 137/826; 516/54; 436/53

(58) Field of Classification Search
USPC ................. 137/807, 826; 556/54; 436/53
See application file for complete search history.

(56) References Cited

U.S. PATENT DOCUMENTS

| | | | |
|---|---|---|---|
| 2,097,692 A | 11/1937 | Fiegel | |
| 2,164,172 A | 6/1939 | Dalton | |
| 2,656,508 A | 10/1953 | Coulter | |
| 2,692,800 A | 10/1954 | Nichols et al. | |
| 2,797,149 A | 6/1957 | Skeggs | |
| 2,879,141 A | 3/1959 | Skeggs | |
| 2,971,700 A | 2/1961 | Peeps | |
| 3,479,141 A | 11/1969 | Smythe et al. | |
| 3,608,821 A | 9/1971 | Simm et al. | |

(Continued)

FOREIGN PATENT DOCUMENTS

| | | |
|---|---|---|
| AU | 2004225691 B2 | 10/2004 |
| CA | 2520548 A1 | 9/2004 |

(Continued)

OTHER PUBLICATIONS

Nguyen N T et al: "Optical detection fordroplet size control in microfluidic droplet-based analysis systems" Sensors and Actuators B, Elsevier Sequoia S.A., Lausanne, CH LNKD-DOI: 10.1016/J. SNB.2005.12.010 vol. 117, No. 2, Oct. 12, 2006, pp. 431-436, XP025112307.*

(Continued)

*Primary Examiner* — John Rivell
*Assistant Examiner* — Matthew W Jellett
(74) *Attorney, Agent, or Firm* — Thomas C. Meyers; Brown Rudnick LLP

(57) ABSTRACT

The invention provides methods for assessing one or more predetermined characteristics or properties of a microfluidic droplet within a microfluidic channel, and regulating one or more fluid flow rates within that channel to selectively alter the predetermined microdroplet characteristic or property using a feedback control.

9 Claims, 11 Drawing Sheets

(56) References Cited

U.S. PATENT DOCUMENTS

| | | |
|---|---|---|
| 3,698,635 A | 10/1972 | Sickles |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,628,040 A | 12/1986 | Green |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |

| Patent | Kind | Date | Inventors |
|---|---|---|---|
| 6,080,295 | A | 6/2000 | Parce et al. |
| 6,086,740 | A | 7/2000 | Kennedy |
| 6,096,495 | A | 8/2000 | Kasai et al. |
| 6,103,537 | A | 8/2000 | Ullman et al. |
| 6,105,571 | A | 8/2000 | Coffee |
| 6,105,877 | A | 8/2000 | Coffee |
| 6,116,516 | A | 9/2000 | Ganan-Calvo |
| 6,118,849 | A | 9/2000 | Tanimori et al. |
| 6,119,953 | A | 9/2000 | Ganan-Calvo et al. |
| 6,120,666 | A | 9/2000 | Jacobson et al. |
| 6,124,388 | A | 9/2000 | Takai et al. |
| 6,124,439 | A | 9/2000 | Friedman et al. |
| 6,130,052 | A | 10/2000 | Van Baren et al. |
| 6,130,098 | A | 10/2000 | Handique et al. |
| 6,137,214 | A | 10/2000 | Raina |
| 6,138,077 | A | 10/2000 | Brenner |
| 6,139,303 | A | 10/2000 | Reed et al. |
| 6,140,053 | A | 10/2000 | Koster |
| 6,143,496 | A | 11/2000 | Brown et al. |
| 6,149,789 | A | 11/2000 | Benecke et al. |
| 6,150,180 | A | 11/2000 | Parce et al. |
| 6,150,516 | A | 11/2000 | Brenner et al. |
| 6,165,778 | A | 12/2000 | Kedar |
| 6,171,796 | B1 | 1/2001 | An et al. |
| 6,171,850 | B1 | 1/2001 | Nagle et al. |
| 6,172,214 | B1 | 1/2001 | Brenner |
| 6,172,218 | B1 | 1/2001 | Brenner |
| 6,174,160 | B1 | 1/2001 | Lee et al. |
| 6,174,469 | B1 | 1/2001 | Ganan-Calvo |
| 6,180,372 | B1 | 1/2001 | Franzen |
| 6,184,012 | B1 | 2/2001 | Neri et al. |
| 6,187,214 | B1 | 2/2001 | Ganan-Calvo |
| 6,189,803 | B1 | 2/2001 | Ganan-Calvo |
| 6,196,525 | B1 | 3/2001 | Ganan-Calvo |
| 6,197,335 | B1 | 3/2001 | Sherman |
| 6,197,835 | B1 | 3/2001 | Ganan-Calvo |
| 6,203,993 | B1 | 3/2001 | Shuber et al. |
| 6,210,396 | B1 | 4/2001 | MacDonald et al. |
| 6,210,891 | B1 | 4/2001 | Nyren et al. |
| 6,210,896 | B1 | 4/2001 | Chan |
| 6,214,558 | B1 | 4/2001 | Shuber et al. |
| 6,221,654 | B1 | 4/2001 | Quake et al. |
| 6,227,466 | B1 | 5/2001 | Hartman et al. |
| 6,234,402 | B1 | 5/2001 | Ganan-Calvo |
| 6,235,383 | B1 | 5/2001 | Hong et al. |
| 6,235,475 | B1 | 5/2001 | Brenner et al. |
| 6,241,159 | B1 | 6/2001 | Ganan-Calvo et al. |
| 6,243,373 | B1 | 6/2001 | Turock |
| 6,248,378 | B1 | 6/2001 | Ganan-Calvo |
| 6,251,661 | B1 | 6/2001 | Urabe et al. |
| 6,252,129 | B1 | 6/2001 | Coffee |
| 6,258,568 | B1 | 7/2001 | Nyren |
| 6,258,858 | B1 | 7/2001 | Nakajima et al. |
| 6,263,222 | B1 | 7/2001 | Diab et al. |
| 6,266,459 | B1 | 7/2001 | Walt et al. |
| 6,267,353 | B1 | 7/2001 | Friedline et al. |
| 6,267,858 | B1 | 7/2001 | Parce et al. |
| 6,268,165 | B1 | 7/2001 | O'Brien |
| 6,268,222 | B1 | 7/2001 | Chandler et al. |
| 6,274,320 | B1 | 8/2001 | Rothberg et al. |
| 6,274,337 | B1 | 8/2001 | Parce et al. |
| 6,294,344 | B1 | 9/2001 | O'Brien |
| 6,296,673 | B1 | 10/2001 | Santarsiero et al. |
| 6,299,145 | B1 | 10/2001 | Ganan-Calvo |
| 6,301,055 | B1 | 10/2001 | Legrand et al. |
| 6,306,659 | B1 | 10/2001 | Parce et al. |
| 6,310,354 | B1 | 10/2001 | Hanninen et al. |
| 6,310,653 | B1 | 10/2001 | Malcolm, Jr. et al. |
| 6,316,208 | B1 | 11/2001 | Roberts et al. |
| 6,316,213 | B1 | 11/2001 | O'Brien |
| 6,318,640 | B1 | 11/2001 | Coffee |
| 6,336,463 | B1 | 1/2002 | Ohta |
| 6,344,325 | B1 | 2/2002 | Quake et al. |
| 6,352,828 | B1 | 3/2002 | Brenner |
| 6,355,193 | B1 | 3/2002 | Stott |
| 6,355,198 | B1 | 3/2002 | Kim et al. |
| 6,357,670 | B2 | 3/2002 | Ganan-Calvo |
| 6,386,463 | B1 | 5/2002 | Ganan-Calvo |
| 6,391,559 | B1 | 5/2002 | Brown et al. |
| 6,394,429 | B2 | 5/2002 | Ganan-Calvo |
| 6,399,339 | B1 | 6/2002 | Wolberg et al. |
| 6,399,389 | B1 | 6/2002 | Parce et al. |
| 6,403,373 | B1 | 6/2002 | Scanlan et al. |
| 6,405,936 | B1 | 6/2002 | Ganan-Calvo |
| 6,408,878 | B2 | 6/2002 | Unger et al. |
| 6,409,832 | B2 | 6/2002 | Weigl et al. |
| 6,429,025 | B1 | 8/2002 | Parce et al. |
| 6,429,148 | B1 | 8/2002 | Chu et al. |
| 6,432,143 | B2 | 8/2002 | Kubiak et al. |
| 6,432,148 | B1 | 8/2002 | Ganan-Calvo |
| 6,432,630 | B1 | 8/2002 | Blankenstein |
| 6,439,103 | B1 | 8/2002 | Miller |
| 6,440,706 | B1 | 8/2002 | Vogelstein et al. |
| 6,450,139 | B1 | 9/2002 | Watanabe |
| 6,450,189 | B1 | 9/2002 | Ganan-Calvo |
| 6,454,193 | B1 | 9/2002 | Busick et al. |
| 6,464,336 | B1 | 10/2002 | Sharma |
| 6,464,886 | B2 | 10/2002 | Ganan-Calvo |
| 6,475,441 | B1 | 11/2002 | Parce et al. |
| 6,481,648 | B1 | 11/2002 | Zimmermann |
| 6,489,103 | B1 | 12/2002 | Griffiths et al. |
| 6,503,933 | B1 | 1/2003 | Moloney et al. |
| 6,506,609 | B1 | 1/2003 | Wada et al. |
| 6,508,988 | B1 | 1/2003 | Van Dam et al. |
| 6,520,425 | B1 | 2/2003 | Reneker |
| 6,524,456 | B1 | 2/2003 | Ramsey et al. |
| 6,540,395 | B2 | 4/2003 | Muhlbauer et al. |
| 6,540,895 | B1 | 4/2003 | Spence et al. |
| 6,551,836 | B1 | 4/2003 | Chow et al. |
| 6,553,944 | B1 | 4/2003 | Allen et al. |
| 6,553,960 | B1 | 4/2003 | Yoshikawa et al. |
| 6,554,202 | B2 | 4/2003 | Ganan-Calvo |
| 6,557,334 | B2 | 5/2003 | Jager |
| 6,557,834 | B2 | 5/2003 | Ganan-Calvo |
| 6,558,944 | B1 | 5/2003 | Parce et al. |
| 6,558,960 | B1 | 5/2003 | Parce et al. |
| 6,560,030 | B2 | 5/2003 | Legrand et al. |
| 6,565,010 | B2 | 5/2003 | Anderson et al. |
| 6,569,631 | B1 | 5/2003 | Pantoliano et al. |
| 6,576,420 | B1 | 6/2003 | Carson et al. |
| 6,591,852 | B1 | 7/2003 | McNeely et al. |
| 6,592,321 | B2 | 7/2003 | Bonker et al. |
| 6,592,821 | B1 | 7/2003 | Wada et al. |
| 6,608,726 | B2 | 8/2003 | Legrand et al. |
| 6,610,499 | B1 | 8/2003 | Fulwyler et al. |
| 6,614,598 | B1 | 9/2003 | Quake et al. |
| 6,627,603 | B1 | 9/2003 | Bibette et al. |
| 6,630,006 | B2 | 10/2003 | Santarsiero et al. |
| 6,630,353 | B1 | 10/2003 | Parce et al. |
| 6,632,619 | B1 | 10/2003 | Harrison et al. |
| 6,638,749 | B1 | 10/2003 | Beckman et al. |
| 6,645,432 | B1 | 11/2003 | Anderson et al. |
| 6,646,253 | B1 | 11/2003 | Rohwer et al. |
| 6,653,626 | B2 | 11/2003 | Fischer et al. |
| 6,656,267 | B2 | 12/2003 | Newman |
| 6,659,370 | B1 | 12/2003 | Inoue |
| 6,660,252 | B2 | 12/2003 | Matathia et al. |
| 6,670,142 | B2 | 12/2003 | Lau et al. |
| 6,679,441 | B1 | 1/2004 | Borra et al. |
| 6,680,178 | B2 | 1/2004 | Harris et al. |
| 6,682,890 | B2 | 1/2004 | Mack et al. |
| 6,717,136 | B2 | 4/2004 | Andersson et al. |
| 6,729,561 | B2 | 5/2004 | Hirae et al. |
| 6,739,036 | B2 | 5/2004 | Koike et al. |
| 6,744,046 | B2 | 6/2004 | Valaskovic et al. |
| 6,752,922 | B2 | 6/2004 | Huang et al. |
| 6,753,147 | B2 | 6/2004 | Vogelstein et al. |
| 6,766,817 | B2 | 7/2004 | da Silva |
| 6,767,194 | B2 | 7/2004 | Jeon et al. |
| 6,767,704 | B2 | 7/2004 | Waldman et al. |
| 6,790,328 | B2 | 9/2004 | Jacobson et al. |
| 6,793,753 | B2 | 9/2004 | Unger et al. |
| 6,797,056 | B2 | 9/2004 | David |
| 6,800,849 | B2 | 10/2004 | Staats |
| 6,806,058 | B2 | 10/2004 | Jesperson et al. |
| 6,808,382 | B2 | 10/2004 | Lanfranchi |
| 6,808,882 | B2 | 10/2004 | Griffiths et al. |
| 6,814,980 | B2 | 11/2004 | Levy et al. |

| | | | | | | |
|---|---|---|---|---|---|---|
| 6,818,395 | B1 | 11/2004 | Quake et al. | 7,507,541 B2 | 3/2009 | Raitano et al. |
| 6,832,787 | B1 | 12/2004 | Renzi | 7,510,707 B2 | 3/2009 | Platica et al. |
| 6,833,242 | B2 | 12/2004 | Quake et al. | 7,510,842 B2 | 3/2009 | Podust et al. |
| 6,841,350 | B2 | 1/2005 | Ogden et al. | 7,514,209 B2 | 4/2009 | Dai et al. |
| 6,872,250 | B2 | 3/2005 | David et al. | 7,514,210 B2 | 4/2009 | Holliger et al. |
| 6,890,487 | B1 | 5/2005 | Sklar et al. | 7,524,633 B2 | 4/2009 | Sidransky |
| 6,897,018 | B1 | 5/2005 | Yuan et al. | 7,527,933 B2 | 5/2009 | Sahin et al. |
| 6,905,844 | B2 | 6/2005 | Kim | 7,537,897 B2 | 5/2009 | Brenner et al. |
| 6,918,404 | B2 | 7/2005 | Dias da Silva | 7,541,383 B2 | 6/2009 | Fu et al. |
| 6,926,313 | B1 | 8/2005 | Renzi | 7,544,473 B2 | 6/2009 | Brenner |
| 6,935,768 | B2 | 8/2005 | Lowe et al. | 7,556,776 B2 | 7/2009 | Fraden et al. |
| 6,936,417 | B2 | 8/2005 | Orntoft | 7,582,446 B2 | 9/2009 | Griffiths et al. |
| 6,942,978 | B1 | 9/2005 | O'Brien | 7,622,081 B2 | 11/2009 | Chou et al. |
| 6,949,342 | B2 | 9/2005 | Golub et al. | 7,632,562 B2 | 12/2009 | Nair et al. |
| 6,960,437 | B2 | 11/2005 | Enzelberger et al. | 7,635,562 B2 | 12/2009 | Harris et al. |
| 6,974,667 | B2 | 12/2005 | Horne et al. | 7,638,276 B2 | 12/2009 | Griffiths et al. |
| 6,998,232 | B1 | 2/2006 | Feinstein et al. | 7,655,435 B2 | 2/2010 | Holliger et al. |
| 7,022,472 | B2 | 4/2006 | Robbins et al. | 7,655,470 B2 | 2/2010 | Ismagilov et al. |
| 7,041,481 | B2 | 5/2006 | Anderson et al. | 7,666,593 B2 | 2/2010 | Lapidus |
| 7,049,072 | B2 | 5/2006 | Seshi | 7,678,565 B2 | 3/2010 | Schurmann-Mader |
| 7,056,674 | B2 | 6/2006 | Baker et al. | 7,691,576 B2 | 4/2010 | Holliger et al. |
| 7,057,026 | B2 | 6/2006 | Barnes et al. | 7,698,287 B2 | 4/2010 | Becker et al. |
| 7,066,586 | B2 | 6/2006 | da Silva | 7,708,949 B2 | 5/2010 | Stone et al. |
| 7,068,874 | B2 | 6/2006 | Wang et al. | 7,718,578 B2 | 5/2010 | Griffiths et al. |
| 7,078,180 | B2 | 7/2006 | Genetta | 7,736,890 B2 | 6/2010 | Sia et al. |
| 7,081,192 | B1 | 7/2006 | Wang et al. | 7,741,130 B2 | 6/2010 | Lee, Jr. et al. |
| 7,081,340 | B2 | 7/2006 | Baker et al. | 7,814,175 B1 | 10/2010 | Chang et al. |
| 7,090,983 | B1 | 8/2006 | Muramatsu et al. | 7,824,889 B2 | 11/2010 | Vogelstein et al. |
| 7,115,230 | B2 | 10/2006 | Sundararajan et al. | 7,897,044 B2 | 3/2011 | Hoyos et al. |
| 7,118,910 | B2 | 10/2006 | Unger et al. | 7,897,341 B2 | 3/2011 | Griffiths et al. |
| 7,129,091 | B2 | 10/2006 | Ismagilov et al. | 7,901,939 B2 | 3/2011 | Ismagilov et al. |
| 7,138,233 | B2 | 11/2006 | Griffiths et al. | 7,968,287 B2 | 6/2011 | Griffiths et al. |
| 7,153,700 | B1 | 12/2006 | Pardee et al. | 8,012,382 B2 | 9/2011 | Kim et al. |
| 7,156,917 | B2 | 1/2007 | Moriyama et al. | 8,153,402 B2 | 4/2012 | Holliger et al. |
| 7,163,801 | B2 | 1/2007 | Reed | 2001/0010338 A1 | 8/2001 | Ganan-Calvo |
| 7,169,560 | B2 | 1/2007 | Lapidus et al. | 2001/0020011 A1 | 9/2001 | Mathiowitz et al. |
| 7,171,311 | B2 | 1/2007 | Dai et al. | 2001/0023078 A1 | 9/2001 | Bawendi et al. |
| 7,198,899 | B2 | 4/2007 | Schleyer et al. | 2001/0029983 A1 | 10/2001 | Unger et al. |
| 7,204,431 | B2 | 4/2007 | Li et al. | 2001/0034031 A1 | 10/2001 | Short et al. |
| 7,229,770 | B1 | 6/2007 | Price et al. | 2001/0041343 A1 | 11/2001 | Pankowsky |
| 7,252,943 | B2 | 8/2007 | Griffiths et al. | 2001/0041344 A1 | 11/2001 | Sepetov et al. |
| 7,267,938 | B2 | 9/2007 | Anderson et al. | 2001/0042793 A1 | 11/2001 | Ganan-Calvo |
| 7,268,167 | B2 | 9/2007 | Higuchi et al. | 2001/0048900 A1 | 12/2001 | Bardell et al. |
| 7,282,337 | B1 | 10/2007 | Harris | 2001/0050881 A1 | 12/2001 | Depaoli et al. |
| 7,291,462 | B2 | 11/2007 | O'Brien et al. | 2002/0004532 A1 | 1/2002 | Matathia et al. |
| 7,294,503 | B2 | 11/2007 | Quake et al. | 2002/0005354 A1 | 1/2002 | Spence et al. |
| 7,300,765 | B2 | 11/2007 | Patel | 2002/0008028 A1 | 1/2002 | Jacobson et al. |
| 7,308,364 | B2 | 12/2007 | Shaughnessy et al. | 2002/0012971 A1 | 1/2002 | Mehta |
| 7,314,721 | B2 | 1/2008 | Gure et al. | 2002/0022038 A1 | 2/2002 | Biatry et al. |
| 7,316,906 | B2 | 1/2008 | Chiorazzi et al. | 2002/0022261 A1 | 2/2002 | Anderson et al. |
| 7,326,529 | B2 | 2/2008 | Ali et al. | 2002/0033422 A1 | 3/2002 | Ganan-Calvo |
| 7,332,280 | B2 | 2/2008 | Levy et al. | 2002/0036139 A1 | 3/2002 | Becker et al. |
| 7,332,590 | B2 | 2/2008 | Nacht et al. | 2002/0058332 A1 | 5/2002 | Quake et al. |
| 7,341,211 | B2 | 3/2008 | Ganan Calvo et al. | 2002/0067800 A1 | 6/2002 | Newman et al. |
| 7,348,142 | B2 | 3/2008 | Wang | 2002/0119459 A1 | 8/2002 | Griffiths |
| 7,358,231 | B1 | 4/2008 | McCaffey et al. | 2002/0143437 A1 | 10/2002 | Handique et al. |
| 7,361,474 | B2 | 4/2008 | Siegler | 2002/0155080 A1 | 10/2002 | Glenn et al. |
| 7,364,862 | B2 | 4/2008 | Ali et al. | 2002/0158027 A1 | 10/2002 | Moon et al. |
| 7,368,255 | B2 | 5/2008 | Bae et al. | 2002/0164271 A1 | 11/2002 | Ho |
| 7,378,233 | B2 | 5/2008 | Sidransky et al. | 2002/0164629 A1 | 11/2002 | Quake et al. |
| 7,378,280 | B2 | 5/2008 | Quake et al. | 2003/0012586 A1 | 1/2003 | Iwata et al. |
| 7,390,463 | B2 | 6/2008 | He et al. | 2003/0015425 A1 | 1/2003 | Bohm et al. |
| 7,393,665 | B2 | 7/2008 | Brenner | 2003/0017579 A1 | 1/2003 | Corn et al. |
| 7,416,851 | B2 | 8/2008 | Davi et al. | 2003/0039169 A1 | 2/2003 | Ehrfeld et al. |
| 7,429,467 | B2 | 9/2008 | Holliger et al. | 2003/0059764 A1 | 3/2003 | Ravkin et al. |
| 7,432,064 | B2 | 10/2008 | Salceda et al. | 2003/0061687 A1 | 4/2003 | Hansen et al. |
| 7,442,507 | B2 | 10/2008 | Polsky et al. | 2003/0064414 A1 | 4/2003 | Benecky et al. |
| 7,449,303 | B2 | 11/2008 | Coignet | 2003/0082795 A1 | 5/2003 | Shuler et al. |
| 7,468,271 | B2 | 12/2008 | Golovchenko et al. | 2003/0124586 A1 | 7/2003 | Griffiths et al. |
| 7,473,530 | B2 | 1/2009 | Huttemann | 2003/0144260 A1 | 7/2003 | Gilon |
| 7,473,531 | B1 | 1/2009 | Domon et al. | 2003/0148544 A1 | 8/2003 | Nie et al. |
| 7,476,506 | B2 | 1/2009 | Schleyer et al. | 2003/0183525 A1 | 10/2003 | Elrod et al. |
| 7,479,370 | B2 | 1/2009 | Coignet | 2003/0224509 A1 | 12/2003 | Moon et al. |
| 7,479,371 | B2 | 1/2009 | Ando et al. | 2003/0229376 A1 | 12/2003 | Sandhu |
| 7,479,376 | B2 | 1/2009 | Waldman et al. | 2003/0230486 A1 | 12/2003 | Chien et al. |
| 7,482,129 | B2 | 1/2009 | Soyupak et al. | 2003/0232356 A1 | 12/2003 | Dooley et al. |
| 7,501,244 | B2 | 3/2009 | Reinhard et al. | 2004/0005582 A1 | 1/2004 | Shipwash |
| 7,504,214 | B2 | 3/2009 | Erlander et al. | 2004/0005594 A1 | 1/2004 | Holliger et al. |
| 7,507,532 | B2 | 3/2009 | Chang et al. | 2004/0018525 A1 | 1/2004 | Wirtz et al. |

| | | |
|---|---|---|
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0069632 A1 | 4/2004 | Ripoll |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0115224 A1 | 6/2004 | Ohno |
| 2004/0134854 A1 | 7/2004 | Higuchi |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagliov et al. |
| 2006/0003347 A1 | 1/2006 | Griffiths et al. |
| 2006/0003429 A1 | 1/2006 | Frost et al. |
| 2006/0003439 A1 | 1/2006 | Ismagliov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagliov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |

| | | | | | | |
|---|---|---|---|---|---|---|
| 2009/0127454 A1 | 5/2009 | Ritchie et al. | | WO | WO-93/22054 | 11/1993 |
| 2009/0127589 A1 | 5/2009 | Rothberg et al. | | WO | WO-93/22055 | 11/1993 |
| 2009/0131353 A1 | 5/2009 | Insel et al. | | WO | WO-93/22058 | 11/1993 |
| 2009/0131543 A1 | 5/2009 | Weitz et al. | | WO | WO-93/22421 | 11/1993 |
| 2009/0191565 A1 | 7/2009 | Lapidus et al. | | WO | WO-94/16332 | 7/1994 |
| 2009/0197248 A1 | 8/2009 | Griffiths et al. | | WO | WO-94/23738 | 10/1994 |
| 2009/0197772 A1 | 8/2009 | Griffiths et al. | | WO | WO-94/24314 | 10/1994 |
| 2009/0246788 A1 | 10/2009 | Albert et al. | | WO | WO-94/26766 | 11/1994 |
| 2009/0325236 A1 | 12/2009 | Griffiths et al. | | WO | WO-98/00705 | 1/1995 |
| 2010/0003687 A1 | 1/2010 | Simen et al. | | WO | WO-95/11922 | 5/1995 |
| 2010/0009353 A1 | 1/2010 | Barnes et al. | | WO | WO-95/19922 | 7/1995 |
| 2010/0022414 A1 | 1/2010 | Link et al. | | WO | WO-95/24929 | 9/1995 |
| 2010/0035252 A1 | 2/2010 | Rothberg et al. | | WO | WO-95/33447 | 12/1995 |
| 2010/0075436 A1 | 3/2010 | Urdea et al. | | WO | WO-96/34112 | 10/1996 |
| 2010/0105112 A1 | 4/2010 | Holtze et al. | | WO | WO-96/38730 | 12/1996 |
| 2010/0111768 A1 | 5/2010 | Banerjee et al. | | WO | WO-96/40062 | 12/1996 |
| 2010/0124759 A1 | 5/2010 | Wang et al. | | WO | WO-96/40723 | 12/1996 |
| 2010/0136544 A1 | 6/2010 | Agresti et al. | | WO | WO-97/00125 | 1/1997 |
| 2010/0137143 A1 | 6/2010 | Rothberg et al. | | WO | WO-97/00442 | 1/1997 |
| 2010/0137163 A1 | 6/2010 | Link et al. | | WO | WO-97/04297 | 2/1997 |
| 2010/0159592 A1 | 6/2010 | Holliger et al. | | WO | WO-97/04748 | 2/1997 |
| 2010/0172803 A1 | 7/2010 | Stone et al. | | WO | WO-97/23140 | 7/1997 |
| 2010/0188073 A1 | 7/2010 | Rothberg et al. | | WO | WO-97/28556 | 8/1997 |
| 2010/0197507 A1 | 8/2010 | Rothberg et al. | | WO | WO-97/39814 | 10/1997 |
| 2010/0210479 A1 | 8/2010 | Griffiths et al. | | WO | WO-97/40141 | 10/1997 |
| 2010/0213628 A1 | 8/2010 | Bausch et al. | | WO | WO-97/45644 | 12/1997 |
| 2010/0233026 A1 | 9/2010 | Ismagliov et al. | | WO | WO-97/47763 | 12/1997 |
| 2010/0255556 A1* | 10/2010 | Hunt et al. ............ 435/173.1 | | WO | WO-98/00231 | 1/1998 |
| 2010/0282617 A1 | 11/2010 | Rothberg et al. | | WO | WO-98/02237 | 1/1998 |
| 2010/0300559 A1 | 12/2010 | Schultz et al. | | WO | WO-98/10267 | 3/1998 |
| 2010/0300895 A1 | 12/2010 | Nobile et al. | | WO | WO-98/13502 | 4/1998 |
| 2010/0301398 A1 | 12/2010 | Rothberg et al. | | WO | WO-98/23733 | 6/1998 |
| 2010/0304982 A1 | 12/2010 | Hinz et al. | | WO | WO-98/31700 | 7/1998 |
| 2011/0000560 A1 | 1/2011 | Miller et al. | | WO | WO-98/33001 | 7/1998 |
| 2011/0114190 A1* | 5/2011 | Wen et al. ............ 137/1 | | WO | WO-98/34120 | 8/1998 |
| 2011/0142734 A1 | 6/2011 | Ismagilov et al. | | WO | WO-98/37186 | 8/1998 |
| 2011/0174622 A1 | 7/2011 | Ismagilov et al. | | WO | WO-98/41869 | 9/1998 |
| 2011/0176966 A1 | 7/2011 | Ismagilov et al. | | WO | WO-98/52691 | 11/1998 |
| 2011/0177494 A1 | 7/2011 | Ismagilov et al. | | WO | WO-98/58085 | 12/1998 |
| 2011/0177586 A1 | 7/2011 | Ismagilov et al. | | WO | WO-99/02671 | 1/1999 |
| 2011/0177609 A1 | 7/2011 | Ismagilov et al. | | WO | WO-99/22858 | 5/1999 |
| 2011/0188717 A1 | 8/2011 | Baudry et al. | | WO | WO-99/28020 | 6/1999 |
| 2011/0190146 A1 | 8/2011 | Boehm et al. | | WO | WO-99/31019 | 6/1999 |
| 2011/0244455 A1 | 10/2011 | Larson et al. | | WO | WO-00/04139 | 7/1999 |
| 2011/0250597 A1 | 10/2011 | Larson et al. | | WO | WO-99/54730 | 10/1999 |
| 2011/0275063 A1 | 11/2011 | Weitz et al. | | WO | WO-99/61888 | 12/1999 |
| 2012/0010098 A1 | 1/2012 | Griffiths et al. | | WO | WO-00/47322 | 2/2000 |
| 2012/0015382 A1 | 1/2012 | Weitz et al. | | WO | WO-00/52455 | 2/2000 |
| 2012/0015822 A1 | 1/2012 | Weitz et al. | | WO | WO-00/40712 | 6/2000 |
| | | | | WO | WO-00/61275 | 10/2000 |
| FOREIGN PATENT DOCUMENTS | | | | WO | WO-00/70080 | 11/2000 |
| CH | 563807 A5 | 7/1975 | | WO | WO-00/76673 | 12/2000 |
| DE | 4308839 C2 | 4/1997 | | WO | WO-01/12327 | 2/2001 |
| EP | 0047130 B1 | 2/1985 | | WO | WO-01/14589 | 3/2001 |
| EP | 0249007 A3 | 3/1991 | | WO | WO-01/18244 | 3/2001 |
| EP | 0476178 A1 | 3/1992 | | WO | WO-01/64332 | 9/2001 |
| EP | 0540281 B1 | 7/1996 | | WO | WO-01/68257 | 9/2001 |
| EP | 0528580 B1 | 12/1996 | | WO | WO-01/69289 | 9/2001 |
| EP | 0895120 | 2/1999 | | WO | WO-01/72431 | 10/2001 |
| EP | 1741482 | 1/2007 | | WO | WO-01/80283 | 10/2001 |
| EP | 2127736 | 12/2009 | | WO | WO-02/18949 | 3/2002 |
| GB | 0114854 | 4/1969 | | WO | WO-02/22869 | 3/2002 |
| GB | 1446998 | 8/1976 | | WO | WO-02/23163 | 3/2002 |
| GB | 2005224 | 4/1979 | | WO | WO-02/31203 | 4/2002 |
| GB | 2047880 | 12/1980 | | WO | WO-02/47665 | 6/2002 |
| GB | 2062225 | 5/1981 | | WO | WO-02/060275 | 8/2002 |
| GB | 2064114 | 6/1981 | | WO | WO-02/078845 | 10/2002 |
| GB | 2097692 A | 11/1982 | | WO | WO-02/103011 | 12/2002 |
| GB | 0221053 | 6/1989 | | WO | WO-02/103363 | 12/2002 |
| JP | 3-232525 | 10/1998 | | WO | WO-03/011443 | 2/2003 |
| JP | 2000271475 | 10/2000 | | WO | WO-03/037302 | 5/2003 |
| WO | WO-84/02000 | 5/1984 | | WO | WO-03/044187 | 5/2003 |
| WO | WO-91/05058 | 4/1991 | | WO | WO-03/078659 | 9/2003 |
| WO | WO-91/07772 | 5/1991 | | WO | WO-03/099843 | 12/2003 |
| WO | WO-92/03734 | 3/1992 | | WO | WO-2004/002627 | 1/2004 |
| WO | WO-92/21746 | 12/1992 | | WO | WO-2004/018497 | 3/2004 |
| WO | WO-93/03151 | 2/1993 | | WO | WO-2004/024917 | 3/2004 |
| WO | WO-93/08278 | 4/1993 | | WO | WO-2004/038363 | 5/2004 |
| WO | WO-93/22053 | 11/1993 | | WO | WO-2004/069849 | 8/2004 |

| | | |
|---|---|---|
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |
| WO | WO-2004/103565 | 12/2004 |
| WO | WO-2005/000970 | 1/2005 |
| WO | WO-2005/002730 | 1/2005 |
| WO | WO-2005/021151 | 3/2005 |
| WO | WO-2005/103106 | 11/2005 |
| WO | WO-2005/118138 | 12/2005 |
| WO | WO-2006/002641 | 1/2006 |
| WO | WO-2006/009657 | 1/2006 |
| WO | WO-2006/027757 | 3/2006 |
| WO | WO-2006/038035 | 4/2006 |
| WO | WO-2006/040551 | 4/2006 |
| WO | WO-2006/040554 | 4/2006 |
| WO | WO-2006/078841 | 7/2006 |
| WO | WO-2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO-2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO 2009005680 A1 * | 1/2009 |
| WO | WO-2009/029229 | 3/2009 |
| WO | WO 2009029229 A2 * | 3/2009 |
| WO | WO-2010/040006 | 4/2010 |
| WO | WO-2010/056728 | 5/2010 |
| WO | WO-2010/151776 | 12/2010 |
| WO | WO-2011/042564 | 4/2011 |

OTHER PUBLICATIONS

Kai-Liang et al: "DEP actuated nanoliter droplet dispensing using feedback control" Lab on a Chip, vol. 9, Dec. 24, 2008, pp. 901-909, XP002584446.*
Adang, A.E. et al., The contribution of combinatorial chemistry to lead generation: an interim analysis, Curr Med Chem 8: 985-998 (2001).
Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).

Angell et al., Silicon micromechanical devices, Scientific American 248:44-55 (1983).
Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin et al., Optical trapping and manipulation of single cells using infrared laser beams, Nature 330:769-771 (1987).
Ashkin and Dziedzic, Optical trapping and manipulation of viruses and bacteria, Science 235(4795):1517-20 (1987).
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of tWO isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR WO rld, PCR Methods and Applications 1(1):5-16 (1991).
Barany, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromotography, 722:55-69 (1999).
Beebe et al., Functional hydrogel structures for autonomous flow control inside microfluidic channels, Nature 404:588-590 (2000).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).

Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRl restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, vol. 247, 2002, pp. 162-166.
Bico, Jose et al., Self-Propelling Slugs, J. Fluid Mech., vol. 467, 2002, pp. 101-127.
Blattner and Dahlberg, RNA synthesis startpoints in bacteriophage lambda: are the promoter and operator transcribed?, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact a Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Product inhibition of alpha-chymotrypsin in reverse micelles. Eur J Biochem 199(1): 95-103 (1991).
Bru, R. et al., Catalytic activity of elastase in reverse micelles, Biochem Mol Bio Int, 31(4):685-92 (1993).
Brummelkamp et al., A system for stable expression of short interfering RNAs in mammalian cells, Science 296(5567):550-3 (2002).
Buckpitt et al., Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon? Drug Discov Today 3:313-322 (1998).
Burns et al., Microfabricated structures for integrated DNA analysis, Proc. Natl. Acad. Sci. USA, May 1996, vol. 93, pp. 5556-5561.
Burns, Mark et al., An Integrated Nanoliter DNA Analysis Device, Science, vol. 282, 1998, pp. 484-487.
Burns, J.R. et al., The Intensification of Rapid Reactions in Multiphase Systems Using Slug Flow in Capillaries, Lab on a Chip, vol. 1, 2001 pp. 10-15.
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).
Chakrabarti, A.C. et al., Production of RNA by a polymerase protein encapsulated within phospholipid vesicles, J Mol Evol, 39(6):555-9 (1994).

Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, vol. 3, No. 2, 2003, pp. 199-201.
Chang, T.M., Recycling of NAD(P) by multienzyme systems immobilized by microencapsulation in artifical cells, Methods Enzymol, 136(67):67-82 (1987).
Chang and Su, Controlled double emulsification utilizing 3D PDMS microchannels, Journal of Micromechanics and Microengineering 18:1-8 (2008).
Chao et al., Control of Concentration and Volume Gradients in Microfluidic Droplet Arrays for Protein Crystallization Screening, 261h Annual International Conference of the IEEE Engineering in Medicine and Biology Society, San Francisco, California Sep. 1-5, (2004).
Chao et al., Droplet Arrays in Microfluidic Channels for Combinatorial Screening Assays, Hilton Head 2004: A Solid State Sensor, Actuator and Microsystems WO rkshop, Hilton Head Island, South Carolina, Jun. 6-10, (2004).
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth 196 (1999), pp. 434-441.
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting The 12th International Conference on Solid State Sensors, Actuators, and Microsystems, Boston, MA Jun. 8-12, 2003 Transducers, 1: 659-662 (2003).
Cheng, Z.,et al, Electro flow focusing inmicrofluidic devices, Microluidics Poster, presented at DBAS, Frontiers in Nanoscience, presented Apr. 10, 2003.
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphptriesterase by rational evolution of active site residues, Biochemistry, 40: 1332-1339 (2001b).
Chetverin and Spirin, Replicable RNA vectors: prospects for cell-free gene amplification, expression, and cloning, Prog Nucleic Acid Res Mol Biol, 51:225-70 (1995).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chamical Society, 73:2018-21 (2001).
Chiu et al., Chemical transformations in individual ultrasmall biomimetic containers, Science, 283: 1892-1895 (1999).
Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).

Cortesi et al., Production of liposheres as carriers for bioactive compounds, Biomateials, 23(11): 2283-2294 (2002).
Craig, D. et al., Fluorescence-based enzymatic assay by capillary electrophoresis laser-induced fluoresence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, S.S. et al., Multiple emulsions as targetable delivery systems, Methods in Enzymology, 149: 51-64 (1987).
Davis, J.A. et al., Deterministic hydrodynamics: Taking blood apart, PNAS 103:14779-14784 (2006).
De-Bashan, L. E. et al., Removal of ammonium and phosphorus ions from synthetic wastewater by the microalgae Chlorella vulgaris coimmobilized in alginate beads with the microalgae growth-promoting bacterium Azospirillum brasilense, Water Research 36 (2002),pp. 2941-2948.
de Gans, B.J. et al., Inkjet printing of polymers: state of the art and future developments, Advanced materials, 16: 203-213 (2004).
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi, N. and Yanagawa, H. STABLE: protein-DNA fusion system for screening of combinatorial protein libraries in vitro, FEBS Lett., 457: 227-230 (1999).
Doi et al., In vitro selection of restriction endonucleases by in vitro compartmentilization, Nucleic Acids Res, 32(12): e95 (2004).
Doman, T.N. et al., Molecular docking and high-throughput screening for novel inhibitors of protein tyrosine phosphatase-1B, J Med Chem, 45: 2213-2221 (2002).
Domling and Ugi, Multicomponent Reactions with Isocyanides, Angew Chem Int Ed 39(18):3168-3210 (2000).
Domling A., Recent advances in isocyanide-based multicomponent chemistry, Curr Opin Chem Biol, 6(3):306-13 (2002).
Dove et al., In Brief, Nature Biotechnology 20:1213 (2002).
Dower et al., High efficiency transformation of E. coli by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Drmanac et al., Sequencing by hybridization: towards an automated sequencing of one million M13 clones arrayed on membranes, Elctrophoresis 13:566-573 (1992).
Dreyfus et al., Ordered and discordered patterns in tw-phase flows in microchannels, Phys Rev Lett 90(14):144505-1-144505-4 (2003).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 2002 pp. 1136-1137.
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech., vol. 401, 1999, pp. 293-310.
Ehrig, T. et al., Green-fluorescent protein mutants with altered fluorescence excitation spectra, Febs Lett, 367(2):163-66 (1995).
Eigen, Wie entsteht information? Prinzipien der selbstorganisation in der biologie, Berichte der punsen-gesellschaft fur physikalische chemi, 80:1059-81 (1976).
Eigen et al., hypercycles and compartments: compartments assists—but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al., Autocatalytic decomposition of cobalt complexes as an indicator system for the determination of trace amounts of cobalt and effectors, Analyst 121:391-394 (1996).
Endo et al. Kinetic determination of trace cobalt by visual autocatalytic indication, Talanta 47:349-353 (1998).
Eow et al., Electrostatic enhancement of coalescence of water droplets in oil: a review of the technology, Chemical Engineeing Journal 85:357-368 (2002).
Eow, et al. Electrostatic and hydrodynamic separation of aqueous drops in a flowing viscous oil, Chemical Eng Proc 41:649-657 (2002).
Eow et al., Electrocoalesce-separators for the separation of aqueous drops from a flowing dielectric viscous liquid, Separation and Purification Tech 29:63-77 (2002).
Eow et al., Motion, deformation and break-up of aqueous drops in oils under high electric ?eld strengths, Chemical Eng Proc 42:259-272 (2003).
Eow et al., The behavior of a liquid-liquid interface and drop-interface coalescence under the in?uence of an electric field, Colloids and Surfaces A: Physiochern. Eng. Aspects 215:101-123 (2003).
Faca et al., A mouse to human search for plasma proteome chagnes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).

Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from Saccharomyces cervisiae by use of an epitope addition method. Mol Cell Biol, 8: 2159-2165 (1988).
Fields, S. And Song, 0., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Industrial Microencapsulation: Polymers for Microcapsule Walls, pp. 1-12 in Encapsulation and Controlled Release, WO odhead Publishing (1993).
Finch, C.A., Encapsulation and controlled release, Spec Publ R Soc Chem, 138:35 (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).
Ganan-Calvo, Generation of Steady Liquid Microthreads and Micron-Sized Monodisperse Sprays and Gas Streams, Phys Rev Lett 80(2):285-288 (1998).
Ganan-Calvo, A.M., Perfectly Monodisperse Microbubbling by Capillary Flow Focusing, Phys Rev Lett 87(27): 274501-1-4 (2001).
Garcia-Ruiz et al., Investigation on protein crystal growth by the gel acupuncture method{, Acta, Cryst., 1994, D50, 99. pp. 484-490.
Garcia-Ruiz et al. A super-saturation wave of protein crystallization, J. Crystal Growth, 2001, v232, pp. 149-155.
Gasperlin et al., The structure elucidation of semisolid w/o emulsion systems containin silicone surfactant, Intl J Pharm, 107:51-6 (1994).
Gasperlin et al., Viscosity prediction of lipophillic semisolid emulsion systems by neural netWO rk modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWO rk: Chemical Amplification Using Nonequilibrium Autocatalytic Reactions Coupled in Time, J. Am. Chem. Soc 126:6327-6331 (2004).

Ghadessy et al., Directed Evolution of Polymerase Function by Compartmentalized Self-Replication, PNAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5{ fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by Comamonas Sp. J546 and Comamonas Sp. J547, Biotechnology and Bioengineering, vol. 59, No. 1, Jul. 5, 1998, pp. 21-27.
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. And Szostak, J.W., Selection of a Ribozyme That Functions as a Superior Template in a Sel£Copying Reaction, Science, 258: 1910-5 (1992).
Gregoriadis, G., Enzyme entrapment in liposomes, Methods Enzymol 44:218-227 (1976).
Griffiths et al., Isolation of high affinity human antibodies directly from large synthetic repertoires, Embo J 13(14):3245-60 (1994).
Griffiths, A.D. et al., Strategies for selection of antibodies by phage display, Curr Opin Biotechnol, 9:102-8 (1998).
Griffiths et al., Man-made enzymes-from design to in vitro compartmentalisation, Curr Opin Biotechnol 11:338-353 (2000).
Griffiths et al., Directed evolution of an extremely fast phosphotriesterase by in vitro compartmentalization, EMBO J, 22:24-35 (2003).
Griffiths, A., and Tawfik, D., Miniaturising the laboratory in emulsion droplets, Trend Biotech 24(9):395-402 (2006).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in Escherichia Coli Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19(11): 3019-3026 (1991).
Haber et al., Activity and spectroscopic properties of bovine liver catalase in sodium bis(2-ethylhexyl) sulfosuccinate/isooctane reverse micelles, Eur J Biochem 217(2): 567-73 (1993).
Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, The effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescenec-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, the EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635 (2001).

Handen, J.S., High-throughput screening- challenges for the future, Drug Discov WOrld, 47-50 (2002).
Handique, K. et al., On-Chip Thermopneumatic Pressure for Discrete Drop Pumping, Analytical Chemistry, vol. 73, 2001, pp. 1831-1838.
Hanes et al., in vitro selection and evolution of functional proteins by using ribosome display, PNAS 94:4937-42 (1997).
Hanes et al., Degradation of porous poly(anhydide-co-imide) microspheres and implication for controlled macromolecule delivery, Biomaterials, 19(1-3): 163-172(1998).
Hansen et al., A robust and scalable microfluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).
Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Hayward et al., Dewetting Instability during the Formation of Polymersomes from BloceCopolymer-Stabilized Double Emulsions, Langmuir, 22(10): 4457-4461 (2006).
He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).
Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71: 22-25 (1949).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for in situ hybridization using CARD amplification, J of Histochem and Cytochem, 46(6):771-77 (1998).
Horton et al., Engineering hybrid genes without the use of restriction enzymes: gene splicing by overlap extension, Gene 77(1), 61-8 (1989).
Hosokawa, Kazuo et al., Handling of Picoliter Liquid Samples in a Poly(dimethylsiloxane)- Based Microfluidic Device, Analytical Chemistry, vol. 71, No. 20, 1999 pp. 4781-4785.
Hsu et al., Comparison of process parameters for microencapsulation of plasmid DNA in poly(D, L-lactic-co-glycolic acid microspheres, J Drug Target, 7:313-23 (1999).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Huang, Z. et al., A sensitive competitive ELISA for 2,4-dinitrophenol using 3,6-fluorescein diphosphate as a fluorogenic substrate, J Immunol Meth, 149:261 (1992).
Huang L. R. et al., Continuous particle separation through deterministic lateral displacement, Science 304(5673):987-990 (2004).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hung et al., Optimization of Droplet Generation by controlling PDMS Surface Hydrophobicity, 2004 ASME International Mechanical Engineering Congrees and RD&D Expo, Nov. 13-19, 2004, Anaheim, CA.
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).
lsmagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Jermutus et al., Recent advances in producing and selecting functional proteins by using cell-free translation, Curr Opin Biotechnol 9(5): 534-48 (1998).
Jestin et al., A Method for the Selection of Catalytic Activity Using Phage Display and Proximity Coupling, Agnew. Chem. Int. Ed. Engi. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, in ELISA and Other Solid Phase Immunoassays, Kemeny et al (ed.), Chapter 4, pp. 85-106 John Wiley (1988).
Johannsson, A., Heterogeneous Enzyme Immunoassays, In Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones, L.J. et al., Quenched BODIPY dye-labeled casein substrates for the assay of protease activity by direct fluorescence measurement, Anal Biochem, 251:144 (1997).
Jones et al. Glowing jellyfish, luminescence and a molecule called coelenterazine, Trends Biotechnol. 17(12):477-81 (1999).

Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial ilms on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij, J.F., et al., High-speed photodamage cell sorting: An evaluation of the ZAPPER prototype, Methods in cell biology, 42: 371-358 (1994).
Keij et al., High-Speed Photodamage Cell Selection Using a Frequency-Doubled Argon Ion Laser, Cytometry, 19(3): 209-216 (1995).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim S. et al, Type II quantum dots: CdTe/CdSe (core/shell) and CdSe/ZnTe (core/shell) heterostructures, J. Am Chem Soc. 125:11466-11467 (2003).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug, A., Gene Regulatory Proteins and Their Interaction with DNA, Ann NY Acad Sci, 758: 143-60 (1995).
Klug and Schwabe, Protein motifs 5. Zinc fingers, FASEB J 9(8):597-604 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Kopp et al., Chemical amplification: continuous flow PCR on a chip, Science, 280:1046-48 (1998).
Koster et al., Drop-based micro?uidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a ?uorocarbon phase, Colloid and Interface Science 8(3):251-258 (2003).
Krafft et al., Synthesis and preliminary data on the biocompatibility and emulsifying properties of perfluoroalkylated phosphoramidates as injectable surfactants, Eur. J. Med. Chem., 26:545-550 (1991).
Kralj et al., Surfactant-enhanced liquid-liquid extraction in microfluidic channels with inline electric-field enhanced coalescence, Lab Chip 5:531-535 (2005).
Kricka and Wilding, Micromachining: a new direction for clinical analyzers, Pure and Applied Chemistry 68(10):1831-1836 (1996).
Kricka and Wilding, Microchip PCR, Anal Bioanal Chem 377(5):820-825 (2003).
Krumdiek, C.L. et al., Solid-phase synthesis of pteroylpolyglutamates, Methods Enzymol, 524-29 (1980).
Kumar, A. et al., Activity and kinetic characteristics of gltathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array-CGH. Genome Res. 13: 294-307 (2003).
Lamprecht et al., pH-sensitive microsphere delivery increases oral bioavailability of calcitonin, Journal of Controlled Release, 98(1):1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).
Lee, et al, Preparation of Silica Paticles Encapsulating Retinol Using 0/W/0 Multiple Emulsions, Journal of Colloid and Interface Science, 240(1): 83-89 (2001).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee et al, Investigating the target recognition of DNA cytosine-5 methyltransferase Hhal by library selection using in vitro compartmentalisation (IVC), Nucleic Acids Res 30:4937-4944 (2002).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of *E coli* transcription factors with core RNA polymerase, J Biol Chem 266(4):2632-8 (1991).
Lesley, S.A., Preparation and use of *E. coli* S-30 extracts, Methods Mol Biol, 37:265-78 (1995).
Leung et al., A method for random mutagenesis of a defined DNA segment using a modified polymerase chain reaction. Technique 1:11-15 (1989).
Li et al., Single-step procedure for labeling DNA strand breaks with lourescein-or BODIPY-conjugated deoxynucleotides: detection of apoptosis and bromodeoxyuridine incorporation. Cytometry 20:172-180 (1995).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).

Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings,A.:Iv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Passive Mixing in a Three-Dimensional Serpentine MicroChannel, J MEMS 9(2):190-197 (2000).
Liu et al., Fabrication and characterization of hydrogel-based microvalves, Mecoelectromech. Syst.11:45-53 (2002).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214: 143-150, 2003).
Lopez-Herrera, et al, {The electrospraying of viscous and non-viscous semi-insulating liquids. Scalilng laws,{ Bulletin of the American Physical Society, vol. 40, No. 12, pp. 2041 (1995).
Lopez-Herrera, et al, {One-Dimensional Simulation of the Breakup of Capillary Jets of Conducting Liquids Application to E.H.D. Spraying,{./. Aerosol. Set, vol. 30, No. 7, pp. 895-912 (1999).
Lopez-Herrera, et al, {Coaxial jets generated from electrified Taylor cones. Scaling laws.,{ Aerosol Science, vol. 34, pp. 535-552 (2003).
Lorenceau et al, Generation of Polymerosomes from Double-Emulsions, Langmuir, 21(20): 9183-9186 (2005).
Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N. M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces A Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
MacLean, D. et al., Glossary of terms used in combinatorial chemistry, Pure Appl. Chem. 71(12):2349-2365 (1999).

Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems A look into next century{s technology or just a fashionable craze?, Trends in Analytical Chemistry 10(5):144-149 (1991).
Mao, Q. et al., Substrate effects on the enzymatic activity of alphachymotrypsin in reverse micelles, Biochem Biophys Res Commun, 178(3):1105-12 (1991).
Mao et al., Kinetic behaviour of alpha-chymotrypsin in reverse micelles: a stopped-flow study, Eur J Biochem 208(1):165-70 (1992).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of *Escherichia Coli* RecA Protein Utilizing 1- anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald et al. Fabrication of microfluidic systems in poly(dimethylsiloxane), Electrophoresis 21(1):27-40 (2000).
McDonald and Whitesides, Poly(dimethylsiloxane) as a material for fabricating microfluidic devices, Account Chem. Res. 35:491-499 (2002).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in *Escherichia coli*: mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).

Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mudler et al., Characterization of tWO human monoclonal antibodies reactive with HLA-B12 and HLA-B60, respectively, raised by in vitro secondary immunization of peripheral blood lymphocytes, Hum. Immunol., 36(3):186 192, 1993.
Mulbry, W.W. et al., Parathion hydrolase specified by the Flavobacterium opd gene: relationshio between the gene and protein. J Bacteriol, 171: 6740-6746 (1989).
Nakano et al., Single-molecule reverse transcription polymerase chain reaction using water-in-oil emulsion, J Biosci Bioeng 99:293-295 (2005).
Nakano et al., Single-molecule PCR using water-in-oil emulsion, J Biotech, 102:117-24 (2003).
Nametkin, S.N. et al., Cell-free translation in reversed micelles, FEB Letters, 309(3):330-32.
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3{-terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol. 2003, v142, pp. 218-231.
Ng, B.L. et al., Factors affecting flow karyotype resolution, Cytometry, Part A 69A: 1028-1036 (2006).
Nihant et al., Polylactide Microparticles Prepared by Double Emulsion/Evaporation Technique. I. Effect of Primary Emulsion Stability, Pharmaceutical Research, 11(10):1479-1484 (1994).
Nisisako, Takasi et al., Droplet Formation in a MicroChannel NetWOrk, Lab on a Chip, vol. 2, 2002, pp. 24-26.
Nisisako et al., Formation of droplets using branch channels in a microfluidic circuit, Proceedings of the SICE Annual Conference. International Session Papers 1262-1264 (2002).
Nisisako et al., Controlled formulation of monodisperse double emulsions in a multiple-phase microluidic system, Sot Matter, 1:23-27 (2005).
Nisisako et al., Microstructuerd Devices for Preparing Controlled Multiple Emulsions. Chem. Eng. Technol 31(8):1091-1098 (2008).
Nissim, A. et al., Antibody fragments from a {single pot{ phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by tWO -step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuous-flow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-versus-library selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theoretical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans l{etat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially De?ned Immobilization of Biomolecules on Glass Surfaces Using 'Caged' Biotin, Bioconjug Chem 7: 317-321 (1996).
Ploem, in Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).

Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil A priori prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equilibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into Sarrachomyeces cervesia by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspeci?c protein adsorption in a plug-based micro?uidic system by controlling inteifacial chemistry using ?uorous-phase surfactants, Anal. Chem. 77:785-796 (2005).
Roberts, J.W.,Termination factor for RNA synthesis, Nature, 224: 1168-74 (1969).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, R.W. Totally in vitro protein selection using mRNA-protein fusions and ribosome display. Curr Opin Chem Biol 3(3), 268-73 (1999).
Roberts & Ja, In vitro selection of nucleic acids and proteins: What are we learning?, Curr Opin Struct Biol 9(4): 521-9 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).

Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong et al., Fabrication of Microchambers Defined by Photopolymerized Hydrogels and Weirs Within Microfluidic Systems: Application to DNA Hybridization, Analytical Chem 74(14):3372-3377 (2002).
Seong and Crooks, Efficient Mixing and Reactions Within Microfluidic Channels Using Microbead-Supported Catalysts, J Am Chem Soc 124(45):13360-1 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321, 2004.
Shtern V, and Hussain F., Hysteresis in swirling jets, J. Fluid Mech. 309:1-44 (1996).
Sia &Whitesides, Micro?uidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).

Slob et al., Structural identifiability of PBPK models: practical consequences for modeling strategies and study designs, Crit Rev Toxicol. 27(3):261-72 (1997).

Smith et al., The synthesis of oligonucleotides containing an aliphatic amino group at the 5{ terminus: synthesis of fluorescent DNA primers for use in DNA sequence analysis, Nucl. Acid Res. 13:2399-2412 (1985).

Smith G.P., Filamentous fusion phage: novel expression vectors that display cloned antigens on the virion surface, Science 228(4705): 1315-7(1985).

Smith et al., Fluorescence detection in automated DNA sequence analysis, Nature 321:674-679 (1986).

Smith et al., Direct mechanical measurements of the elasticity of single DNA molecules by using magnetic beads, Science 258(5085):1122-1126 (1992).

Smith et al., Phage display, Chemical Reviews 97(2), 391-410 (1997).

Smyth et al., Markers of apoptosis: methods for elucidating the mechanism of apoptotic cell death from the nervous system, Biotechniques 32:648-665 (2000).

Sohn, et al, Capacitance cytometry: Measuring biological cells one by one, PNAS 97(20):10687-10690 (2000).

Somasundaram and Ramalingam, Gain studies of Rhodamine 6G dye doped polymer laser, J Photochem Photobiol 125(1-3):93-98 (1999).

Song, H. and lsmagilov, R.F., Millisecond kinetics on a microluidic chip using nanoliters of reagents, J Am Chem Soc. 125: 14613-14619 (2003).

Song et al., A microfluidic system for controlling reaction netWO rks in time, Angew. Chem. Int. Ed. 42(7):768-772 (2003).

Song et al., Experimental Test of Scaling of Mixing by Chaotic Advection in Droplets Moving Through Microfluidic Channels, App Phy Lett 83(22):4664-4666 (2003).

Soni and Meller, Progress toward ultrafast DNA sequencing using solid-state nanopores, Clin Chem 53:1996-2001 (2007).

Soumillion et al., Selection of B-lactomase on filamentous bacteriophage by catalytic activity, J Mol Biol, 237:415-22 (1994).

Soumillion et al., Novel concepts for the selection of catalytic activity. Curr Opin Biotechnol 12:387-394 (2001).

Sproat et al., The synthesis of protected 5'-mercapto-2',5'-dideoxyribonucleoside-3-0- phosphorainidites, uses of 5-mercapto-oligodeoxyribonucleotides, Nucleic Acids Res 15:4837-4848 (1987).

Stauber, et a., Rapid generation of monoclonal antibody-secreting hybridomas against African horse sickness virus by in vitro immunization and the fusion/cloning technique, J. Immunol. Meth 161(2):157-168 (1993).

Stemmer, W.P., DNA shuffling by random fragmentation and reassembly: in vitro recombination for molecular evolution. PNAS 91(22):10747-51(1994).

Stemmer, W.P., Rapid evolution of a protein in vitro by DNA shuffling, Nature 370(6488):389-91 (1994).

Stober et al., Controlled growth of monodisperse silica spheres in the micron size range, J Colloid and Interface Sci 26(1):62-69 (1968).

Stofko, H.R. et al., A single step purification for recombinant proteins. Characterization of microtube associated protein (MAP2) fragment which associates with the type II cAMP-dependent protein kinase, Febs Lett 302: 274-278 (1992).

Strizhkov et al., PCR amplification on a microarray of gel-immobilized oligonucleotides: Detection of bacterial toxin- and drug- resistant genes and their mutations, BioTechniques 29(4):844-857 (2000).

Stroock et al., Chaotic mixer for microchannels, Science 295(5555):647-651 (2002).

Studer et al., Fluorous Synthesis: A Fluorous-Phase Strategy for Improving Separation Efficiency in Organic Synthesis, Science 275: 823-826 (1997).

Sugiura et al., Effect of Channel Structure on MicroChannel Emuisification, Langmuir 18:5708-5712 (2002).

Sugiura et al., Interfacial tension driven monodispersed droplet formation from mtcrofabricated channel array Langmuir, 17: 5562-5566 (2001).

Sundberg et al., Spatially-Addressable Immobilisation of Macromolecules on Solid Supports, J. Am. Chem. Soc, 117:12050-12057 (1995).

Suzuki et al., Random mutagenesis of thermus aquaticus DNA polmerase I: concordance of immutable sites in vivo with the crystal structure, PNAS USA, 93:96701-9675 (1996).

Szostak, J.W., In vitro selection of functional nucleic acids. Ann. Rev. Biochem. 68, 611-647 (1999).

Takayama et al., Patterning Cells and Their Environments Using Multiple Laminar Fluid Flows in Capillary NetWO rks, PNAS 96:5545-5548 (1999).

Takeuchi et al., An Axisymmetric Flow-Focusing Microfluidic Device, Adv. Mater 17(8):1067-1072 (2005).

Tan, Y.C., Monodisperse Droplet Emulsions in Co-Flow Microfluidic Channels, Micro TAS, Lake Tahoe (2003).

Tan, Y.C., Microfluidic Liposome Generation from Monodisperse Droplet Emulsion-Towards the Realization of Artificial Cells, Summer Bioengineering Conference, Florida (2003).

Tan et al., Controlled Fission of Droplet Emulsions in Bifurcating Microfluidic Channels, Transducers Boston (2003).

Tan et al., Design of microluidic channel geometries for the control of droplet volume, chemical concentration, and sorting, Lab Chip, 4(4): 292-298 (2004).

Tan et al., Monodispersed micro?uidic droplet generation by shear focusing micro?uidic device, Sensors and Actuators 114:350-356 (2006).

Tanaka et al., Ethanol Production from Starch by a Coimmobilized Mixed Culture System of Aspergillus awamori and Zymomonas mobilis, Biotechnol Bioeng XXVII:1761-1768 (1986).

Tang et al., A multi-color fast-switching microfluidic droplet dye laser, Lab Chip 9:2767-2771 (2009).

Taniguchi et al., Chemical Reactions in Microdroplets by Electrostatic Manipulation of Droplets in Liquid Media, Lab on a Chip 2:19-23 (2002).

Tawfik et al., catELISA: a facile general route to catalytic antibodies, PNAS 90(2):373-7 (1993).

Tawfik, D.S. et al., 1,8-diabycyclo[5.4.0]undecane mediated transesterification of p-nitrophenyl phosphonates- a novel route to phosphono esters, Synthesis-Stuttgart, 10: 968-972 (1993).

Tawfik et al., Efficient and selective p-nitrophenyl-ester=hydrolyzing antibodies elicited by a p-nitrobenzyl phosphonate hapten, Eur J Biochem, 244:619-26 (1997).

Tawfik et al., Man-made cell-like compartments for molecular evolution, Nature Biotechnology, 7(16):652-56 (1998).

Taylor et al., Characterization of chemisorbed monolayers by surface potential measurments, J. Phys. D. Appl. Phys. 24:1443 (1991).

Tchagang et al., Early detection of ovarian cancer using group biomarkers, Mol Cancer Ther 7:27-37 (2008).

Tencza et al., Development of a Fluorescence Polarization-Based Diagnostic Assay for Equine Infectious Anemia Virus, J Clinical Microbiol 38(5):1854-185 (2000).

Terray, et al, Fabrication of linear colloidal structures for microfluidic applications, Applied Phys Lett 81(9):1555-1557 (2002).

Terray et al., Microluidic Control Using Colloidal Devices,Science, 296(5574):1841-1844 (2002).

Tewhey et al., Microdroplet-based PCR amplification for large scale targeted sequencing, Nat Biotechnol 27(11):1025-1031 (2009).

Thompson, L.F., Introduction to Lithography, ACS Symposium Series 219:1-13, (1983).

Thorsen et al., Dynamic pattern formation in a vesicle-generating microfluidic device, Phys Rev Lett 86(18):4163-4166 (2001).

Thorsen et al., Microfluidic Large-Scale Integration, Science 298:580-584 (2002).

Tice et al., Formation of droplets and mixing in multiphase microfluidics at low values of the reynolds and the capillary numbers, Langmuir 19:9127-9133 (2003).

Tice et al., Effects of viscosity on droplet formation and mixing in microfluidic channels, Analytica Chimica Acta 507:73-77 (2004).

Titomanlio et al., Capillary experiments of flow induced crystallization of Hope{, AIChe Journal, 1990, v36, No. 1, pp. 13-18.

Tleugabulova et al., Evaluating formation and growth mechanisms of silica particles using fluorescence anisotropy decay analysis, Langmuir 20(14):5924-5932 (2004).

Tokatlidis et al., Nascent chains: folding and chaperone intraction during elongation on ribosomes, Philos Trans R Soc Lond B Biol Sci, 348:89-95 (1995).

Tokeshi et al., Continuous-Flow Chemical Processing on a Microchip by Combining Microunit Operations and a Multiphase Flow NetWO rk, Anal Chem 74(7):1565-1571 (2002).

Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).

Tramontano, A., Catalytic antibodies, Science 234(4783):1566-70 (1986).

Trindade, T., Nanocrystalline semiconductors: synthesis, properties, and perspectives, Chem. Mat. 13:3843-3858 (2001).

Tripet, B. et al., Engineering a de novo-designed coiled-coil heterodimerization domain off the rapid detection, purification and characterization of recombinantly expressed peptides and proteins, Protein Engng., 9:1029-42 (1996).

Tuerk, C. And Gold, L., Systematic Evolution of Ligands by Exponentid Enrichment: RNA Ligands to Bacteriophage T4 DNA Polymerase, Science, 249:505-10 (1990).

Umbanhowar et al., Monodisperse Emulsion Generation via Drop Break Off in a Coflowing Stream, Langmuir 16(2):347-351 (2000).

Unger et al., Monolithic microfabricated valves and pumps by multylayer soft lithography, Science 288(5463):113-116 (2000).

Utada, A. et al., Monodisperse double emulsions generated from a microcapillary device, Science, 308:537-541 (2005).

Vainshtein et al., Peptide rescue of an N-terminal truncation of the stoffel fragment of Taq DNA polymerase, Protein Science, 5:1785-92 (1996).

Van Bockstaele et al., Prognostic markers in chronic lymphocytic leukemia: a comprehensive review, Blood Rev 23(1):25-47 (2009).

Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.

Van Dilla et al., Cell Microfluorometry: A Method for Rapid Fluorescence Measurement, Science 163(3872):1213-1214 (1969).

Vanhooke et al., Three-dimensional structure of the zinc-containing phosphotrieesterase with the bound substrate analog diethy 4-methylbenzylphosphonate, Biochemistry 35:6020-6025 (1996).

Varga, J.M. et al., Mechanism of allergic cross-reactions-I. Multispecific binding of ligands to a mouse monoclonal anti-DNP IgE antibody. Mol Immunol 28(6), 641-54 (1991).

Vary, A homogeneous nucleic acid hybridization assay based on strand displacement, Nucl Acids Res 15(17):6883-6897 (1987).

Venkateswaran et al., Production of Anti-Fibroblast Growth Factor Receptor Monoclonal Antibodies by in Vitro Immunization, Hybirdoma, 11(6):729-739 (1992).

Venter et al., The sequence of the human genome, Science 291(5507):1304-51 (2001).

Vogelstein et al., Digital PCR, PNAS 96(16):9236-9241 (1999).

Voss, E.W., Kinetic measurements of molecular interactions by spectrofluorometry, J Mol Recognit, 6:51-58 (1993).

Wahler, D. et al., Novel methods for biocatalyst screening. Curr Opin Chem Biol, 5: 152-158 (2001).

Walde, P. et al., Structure and activity of trypsin in reverse micelles, Eur J Biochem, 173(2):401-9 (1988).

Walde, P. et al., Spectroscopic and kinetic studies of lipases solubilized in reverse micelles, Biochemistry, 32(15):4029-34 (1993).

Walker et al., Strand displacement amplification—an isothermal, in vitro DNA amplification technique, Nucleic Acid Res, 20(7):1691-6 (1992).

Walker et al., Isothermal in vitro amplification of DNA by a restriction enzyme/DNA polymerase system, PNAS 89(1):392-6 (1992).

Wang, A.M. et al., Quantitation of mRNA by the polymerase chain reaction. Proc natl Acad Sci USA 86(24), 9717-21 (1989).

Wang, G.T. et al., Design and synthesis of new fluorogenic HIV protease substrates based on resonance energy transfer, Tetrahedron Lett., 31:6493 (1990).

Wang et al., Preparation of Titania Particles Utilizing the Insoluble Phase Interface in a MicroChannel Reactor, Chemical Communications 14:1462-1463 (2002).

Wang et al., DEP actuated nanoliter droplet dispensing using feedback control, Lab on a Chip 9:901-909 (2008).

Warburton, B., Microcapsules for Multiple Emulsions, Encapsulation and Controlled Release, Spec Publ R Soc Chem, 35-51 (1993).

Weil. et al., Selective and accurate initiation of transcription at the Ad2 major late promotor in a soluble system dependent on purified RNA polymerase II and DNA, Cell, 18(2):469-84 (1979).

Wetmur et al., Molecular haplotyping by linking emulsion PCR: analysis of paraoxonase 1 haplotypes and phenotypes, Nucleic Acids Res 33(8):2615- 2619 (2005).

Wick et al., Enzyme-containing liposomes can endogenously produce membrane-constituting lipids, Chem Biol 3(4):277-85 (1996).

Widersten and Mannervik, Glutathione Transferases with Novel Active Sites Isolated by Phage Display from a Library of Random Mutants, J Mol Biol 250(2):115-22 (1995).

Wiggins et al., Foundations of chaotic mixing, Philos Transact A Math Phys Eng Sci 362(1818):937-70 (2004).

Williams et al., Methotrexate, a high-affinity pseudosubstrate of dihydrofolate reductase, Biochemistry, 18(12):2567-73 (1979).

Williams et al., Amplification of complex gene libraries by emulsion PCR, Nature Methods 3(7):545-550 (2006).

Wilson, D.S. And Szostak, J.W., in vitro selection of functional nucleic acids, Ann. Rev. Biochem. 68: 611-647 (1999).

Winter et al., Making antibodies by phage display technology, Annu Rev Immunol 12:433-55 (1994).

Wittrup, K.D., Protein engineering by cell-surface display. Curr Opin Biotechnology, 12: 395-399 (2001).

Wolff et al., Integrating advanced functionality in a microfabricated high-throughput fluorescent-activated cell sorter, Lab Chip, 3(1): 22-27 (2003).

Wronski et al., Two-color, fluorescence-based microplate assay for apoptosis detection. Biotechniques, 32:666-668 (2002).

Wu et al., The ligation amplification reaction (LAR)-amplification of specific DNA sequences using sequential rounds of template-dependent ligation, Genomics 4(4):560-9 (1989).

Wyatt et al., Synthesis and purification of large amounts of RNA oligonucleotides, Biotechniques 11(6):764-9 (1991).

Xia and Whitesides, Soft Lithography, Angew. Chem. Int. Ed. 37:550-575 (1998).

Xia and Whitesides, Soft Lithography, Ann. Rev. Mat. Sci. 28:153-184 (1998).

Xu, S. et al., Generation of monodisperse particles by using microfluidics: control over size, shape, and composition, Angew. Chem. Int. Ed. 44:724-728 (2005).

Yamagishi, J. et al., Mutational analysis of structure-activity relationships in human tumor necrosis factor-alpha, Protein Eng, 3:713-9 (1990).

Yamaguchi et al., Insulin-loaded biodegradable PLGA microcapsules: initial burst release controlled by hydrophilic additives, Journal of Controlled Release, 81(3): 235-249 (2002).

Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).

Yershov et al., DNA analysis and diagnostics on oligonucleotide microchips, PNAS 93(10):4913-4918 (1996).

Yonezawa et al., DNA display for in vitro selection of diverse peptide libraries, Nucleic Acids Research, 31(19): e118 (2203).

Yu et al., Specific inhibition of PCR by Non-Extendable Oligonucleotides Using a 5' to 3' Exonuclease-Defcient DNA Polymerase, Biotechniques 23(4):714-6, 718-20 (1997).

Yu et al. Responsive biomimetic hydrogel valve for microfluidics. Appl. Phys. Lett 78:2589-2591 (2001).

Yu et al., Quantum dot and silica nanoparticle doped polymer optical fibers, Optics Express 15(16):9989-9994 (2007).

Zaccolo, M. et al., An approach to random mutagenesis of DNA using mixtures of triphosphate derivatives of nucleoside analogues. J Mol Biol 255(4):589-603 (1996).

Zakrzewski, S.F., Preparation of tritiated dihydrofolic acid of high specific activity, Methods Enzymol, 539 (1980).

Zaug and Cech, The Tetrahymena intervening sequence ribonucleic acid enzyme is a phosphotransferase and an acid phosphatase, Biochemistry 25(16):4478-82 (1986).

Zaug et al., The Tetrahymena ribozyme acts like an RNA restriction endonuclease, Nature 324(6096):429-33 (1986).

Zaug and Cech, The intervening sequence RNA of Tetrahymena is an enzyme, Science 231(4737):470-5 (1986).

Zhang, Z.Y., Substrate specificity of the protein tyrosine phosphatases, PNAS 90: 4446-4450 (1993).

Zhang et al., A Simple Statistical Parameter for Use in Evaluation and Validation of High Throughput Screening Assays, Journal of Biomolecular Screening, 4(2): 67-73 (1999).

Zhao, H. et al., Molecular evolution by staggered extension process (StEP) in vitro recombination. Nat Biotechnol 16(3):258-61 (1998).

Zhao, B. et al., Control and Applications of Immiscible Liquids in Microchannels, J. Am. Chem. Soc, vol. 124:5284-5285 (2002).

Zheng et al., Screening of Protein Crystallization Conditions on a Microfluidic Chip Using Nanoliter-Size Droplets, J Am Chem Soc 125(37):11170-11171 (2003).

Zheng et al., Formation of Droplets of Alternating Composition in Microfluidic Channels and Applications to Indexing of Concentrations in Droplet-Based /Assays, Anal. Chem., 2004, v. 76, pp. 4977-4982.

Zheng et al., a Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., pp. 1-4, 2004.

Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).

Zimmermann et al., Dielectric Breakdown of Cell Membranes, Biophys J 14(11):881-889 (1974).

Zimmermann et al., Microscale Production of Hybridomas by Hypo-Osmolar Electrofusion, Hum. Antibod. Hybridomas, 3(1): 14-18 (1992).

Zubay, G., In vitro synthesis of protein in microbial systems, Annu Rev Genet, 7: 267-87 (1973).

Zubay, G., The isolation and properties of CAP, the catabolite gene activator, Methods Enzymol, 65: 856-77 (1980).

Zuckermann, R. et al., Efficient Methods for Attachment of Thiol-Specific Probes to the 3{-end of Synthetic Oligodeoxyribonucleotides, Nucleic Acids Res. 15:5305-5321 (1987).

* cited by examiner

MANIPULATION OF MICROFLUIDIC DROPLETS

CROSS-REFERENCE TO RELATED APPLICATIONS

This application claims the benefit of U.S. Provisional Application No. 61/162,521, filed Mar. 23, 2009, the contents of which are incorporated herein by reference in their entirety.

FIELD OF THE INVENTION

The invention relates to the control and manipulation of microdroplets within microchannels.

BACKGROUND OF THE INVENTION

Methods for generating microdroplets of a uniform volume at a regular frequency are well known in the art. However, sample to sample variations in viscosity, viscoelasticity, surface tension or other physical properties of the sample fluid coming from, but not limited to, the inclusion of polymers, detergents, proteins, cells, nucleic acids or buffering solutions, influence the droplet size and volume and, hence, the frequency of generation in an unpredictable way. Thus, the same nozzle on the same microfluidic substrate with same carrier fluid, but a different dispersed fluid will result in a different droplet volume at a different frequency. These limitations also have an impact on the extent to which volumes can be reproducibly combined. Together with typical variations in pump flow rate precision and variations in channel dimensions, microfluidic systems are severely limited without a means to compensate on a run-to-run basis.

As a result of the above factors, current microdroplet technologies cannot efficiently or reliably be used for applications involving combining droplets of different species at high frequencies. Consequently, there is a need in the art for methods of precise control, manipulation and regulation of droplet frequency generation, frequency of library droplet introduction and droplet volume.

SUMMARY OF THE INVENTION

The present invention provides a feedback control system for microfluidic droplet manipulation comprising: providing a microfluidic system comprising at least one microfluidic channel containing at least one fluidic droplet; detecting at least one predetermined characteristics of said fluidic droplet at one or more positions within said microfluidic channel; assessing said predetermined characteristic using an image sensor; and transmitting said assessment from said image sensor to a feedback controller, wherein said feedback controller adjusts a flow rate of one or more fluids, thereby manipulating said fluidic droplet within said microfluidic channel. The detecting at least one predetermined characteristics of said fluidic droplet at one or more positions within said microfluidic channel can further comprises acquiring a plurality of images of said fluidic droplet at a plurality of time points within said microfluidic channel, wherein said plurality of images comprises an image set. The system can further include: assessing said predetermined characteristic of said fluidic droplet in said microfluidic channel, within each image set, using an image sensor; comparing said assessment of said predetermined characteristic of said fluidic droplet in each image set; and determining an average assessment of said predetermined characteristic of said fluidic droplet; wherein said feedback controller adjusts a flow rate of one or more fluids, thereby increasing the accuracy of the assessment.

The predetermined characteristic can be droplet volume, droplet generation rate, droplet arrival frequency, droplet release rate, or total droplet count. The one or more fluids can be a carrier fluid or a drive fluid.

The present invention also provides a feedback control system for manipulating microfluidic droplet pairing ratios comprising: providing a microfluidic system comprising at least one microfluidic channel; producing a first plurality of fluidic droplets within said microfluidic channel at a first frequency; producing a second plurality of fluidic droplets within said microfluidic channel at a second frequency, wherein at least one fluidic droplet from said first plurality and at least one fluidic droplet from said second plurality are paired; assessing said first frequency and said second frequency using an image sensor; and transmitting said assessment of said first and said second frequency from the image sensor to a feedback controller; wherein said feedback controller adjusts a flow rate of one or more fluids to provide a desired frequency ratio of said first to said second plurality of droplets, thereby manipulating the pairing ratios of said first and second pluralities of fluidic droplets within said microfluidic channel. The first plurality of fluidic droplets and the second plurality of fluidic droplets were introduced at the same frequency and wherein said feedback controller adjusts a flow rate of one or more fluids to maintain said first and said second frequency at the same frequency.

The first and second pluralities of fluidic droplets can differ in size, color, refractive index, or extinction coefficient. The first and second pluralities of fluidic droplets can contain a different biological, biochemical, or chemical entity. The desired frequency ratio of the first plurality of droplets to the second plurality of droplets can be 1:1, 1:2, 1:3, 1:4, 1:5, 1:6, 1:7, 1:8, 1:9, or 1:10. Preferably, the desired frequency ratio of the first plurality of droplets to the second plurality of droplets is 1:1.

The present invention also provides a feedback control system for controlling microfluidic droplet count comprising: providing a microfluidic system comprising at least one microfluidic channel; producing at least a first plurality of fluidic droplets within said microfluidic channel at a first frequency; assessing said first frequency using an image sensor; determining the time required to produce a predetermined amount of fluidic droplets based upon said frequency assessment; and transmitting said assessment to a feedback controller, wherein said feedback controller stops said introduction of said droplets after said determined time, thereby controlling the microfluidic droplet count.

The present invention also provides a feedback control system for independently controlling microfluidic droplet volume and frequency comprising: providing a microfluidic system comprising at least one microfluidic channel; producing a plurality of fluidic droplets within a carrier fluid within said microfluidic channel using a drive fluid; assessing the frequency, volume, and flow rate of said plurality of droplets using an image sensor; transmitting said assessed frequencies, volumes, and flow rates of the plurality of droplets from said image sensor to a feedback controller; adjusting a flow rate of the carrier fluid using said feedback controller to attain a predetermined droplet frequency set point; and adjusting a flow rate of the drive fluid using said feedback controller to attain a predetermined droplet volume set point; wherein said feedback control system independently determines and controls microfluidic droplet frequency and volume. The plurality of fluidic droplets can be generated within the microfluidic channel. The plurality of fluidic droplets can be pre-formed and introduced to the microfluidic channel.

The invention provides a feedback control system for microfluidic droplet manipulation including: (a) detecting one or more predetermined characteristics of a droplet at one or more positions within a microfluidic channel; (b) assessing the predetermined characteristic using an image sensor; and (c) transmitting the assessment from the image sensor to a feedback controller, wherein the feedback controller adjusts a flow rate of one or more fluids, thereby manipulating the droplet within the microfluidic channel. In one aspect of this system, the predetermined characteristic is droplet volume, droplet generation rate, droplet release rate, or total droplet count. Preferably, the predetermined characteristic is droplet volume. In another aspect of this system, the fluid is a carrier fluid or a drive fluid.

The invention also provides a feedback control system for manipulating microfluidic droplet pairing ratios including: (a) producing a first plurality of droplets within a microfluidic channel at a frequency; (b) assessing the frequency of the first-plurality of droplets using an image sensor; (c) producing a second plurality of droplets within a microfluidic channel at the same frequency as the first plurality of droplets; (d) assessing the frequency of the second plurality of droplets using an image sensor; and (e) transmitting the frequencies of the first and second pluralities of droplets from the image sensor to a feedback controller; wherein the feedback controller adjusts a flow rate of one or more fluids to maintain the first and second pluralities of droplets at identical frequencies, thereby manipulating the pairing ratios of the first and second pluralities of droplets within the microfluidic channel. In one aspect of this system, the first and second pluralities of droplets differ in size, color, refractive index, or extinction coefficient. Alternatively, or in addition, the first and second pluralities of droplets contain a different biological, biochemical, or chemical entity. In another aspect of this system, the fluid is a carrier fluid or a drive fluid.

Furthermore, the invention provides a feedback control system for assessing and manipulating a predetermined characteristic of a microfluidic droplet including: (a) acquiring a plurality of images of a droplet at a plurality of time points within a microfluidic channel, wherein said plurality of images comprises an image set; (b) assessing the predetermined characteristic of the droplet in the microfluidic channel using an image sensor; and (c) transmitting the assessment from the image sensor to a feedback controller, wherein the feedback controller adjusts a flow rate of one or more fluids, thereby manipulating the predetermined characteristic of the droplet within the microfluidic channel. In one aspect, this system further includes: (a) acquiring a plurality of image sets at a plurality of time points; (b) assessing the predetermined characteristic of the droplet in the microfluidic channel, within each image set, using an image sensor; (c) comparing the assessment of the predetermined characteristic of the droplet in each image set; and (d) determining an average assessment of the predetermined characteristic of the droplet; wherein the feedback controller adjusts a flow rate of one or more fluids, thereby increasing the accuracy of the assessment. In another aspect of this system, the predetermined characteristic is droplet arrival frequency or droplet volume. Moreover, the fluid of this system is a carrier fluid or a drive fluid.

The invention provides a feedback control system for independently controlling microfluidic droplet volume and frequency including: (a) producing a plurality of droplets within a microfluidic channel; (b) assessing the droplet frequency, volume, and flow rate of the plurality of droplets using an image sensor; (c) transmitting the frequencies, volumes, and flow rates of the plurality of droplets from the image sensor to a feedback controller; (d) adjusting a flow rate of the carrier fluid using a feedback controller to attain a predetermined droplet frequency set point; and (e) adjusting a flow rate of a drive fluid using a feedback controller to attain a predetermined droplet volume set point; wherein the feedback control system independently determines microfluidic droplet frequency and volume.

The invention further provides a feedback control system for manipulating microfluidic droplet pairing ratios including: (a) producing a first plurality of droplets within a microfluidic channel at a frequency; (b) assessing the frequency of the first-plurality of droplets using an image sensor; (c) producing a second plurality of droplets within a microfluidic channel at a second frequency; (d) assessing the frequency of the second plurality of droplets using an image sensor; and (e) transmitting the frequencies of the first and second pluralities of droplets from the image sensor to a feedback controller; wherein the feedback controller adjusts a flow rate of one or more fluids to produce a desired frequency ratio of the first to the second plurality of droplets, thereby manipulating the pairing ratios of the first and second pluralities of droplets within the microfluidic channel. In one aspect of this system, the desired frequency ratio of the first plurality of droplets to the second plurality of droplets is 1:1. Alternatively, the desired frequency ratio of the first plurality of droplets to the second plurality of droplets is selected from the group consisting of 1:1, 1:2, 1:3, 1:4, 1:5, 1:6, 1:7, 1:8, 1:9, and 1:10. Alternatively, or in addition, each droplet of the first plurality of droplets comprises a single element of a genomic library and each droplet the second plurality of droplets comprises a single primer pair.

The invention provides a feedback control system for controlling microfluidic droplet count including: (a) producing at least a first plurality of droplets within a microfluidic channel at a frequency; (b) assessing the frequency of the first-plurality of droplets using an image sensor; (c) determining the time required to produce a predetermined amount of droplets based upon the frequency assessment; and (d) transmitting the assessment to a feedback controller, wherein the feedback controller stops production of the droplets after the determined time, thereby controlling the microfluidic droplet count.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

Figure 1:
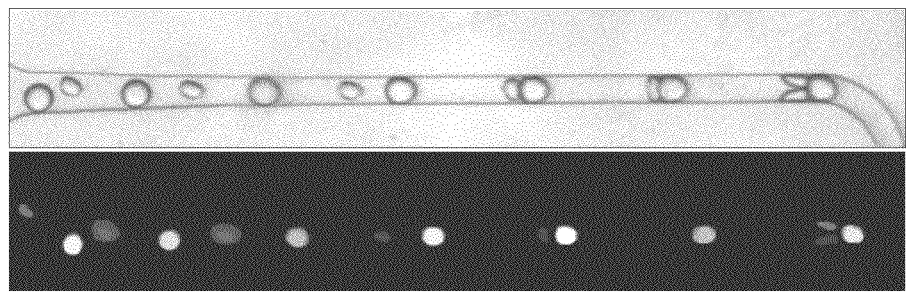
FIG. 1 is a photograph of a series of images of two fluidic droplets paired within a microfluidic channel. One droplet is from a first plurality of droplets at one size and the second droplet is from a second plurality of droplets and a different size than the droplet from the first plurality. This representative image shows the droplet from the first plurality and the droplet from the second plurality paired in a 1:1 ratio. The top panel shows droplets in the region of interest (ROI) and the bottom panel shows the corresponding "contour accumulator image," in which the grey level intensity corresponds to the number of times each pixel was added to the accumulator image. In the bottom panel, all other pixels were assigned the value "0", which is shown as black.

The methods of the present invention provide precise and highly regulated control of microfluidic droplet movement and interaction within a microfluidic channel. The invention provides a feedback control system for microfluidic droplet manipulation including: (a) providing a microfluidic system comprising at least one microfluidic channel containing at least one fluidic droplet; (b) detecting at least one predetermined characteristics of the fluidic droplet at one or more positions within the microfluidic channel; (c) assessing the predetermined characteristic using an image sensor; and (d) transmitting the assessment from the image sensor to a feedback controller, wherein the feedback controller adjusts a flow rate of one or more fluids, thereby manipulating the fluidic droplet within the microfluidic channel. The manipulating or controlling a droplet or a plurality of droplets within a microfluidic channel includes, but is not limited to, manipulating an absolute or relative droplet volume, a droplet pairing ratio, a droplet frequency, a droplet frequency ratio, the number of droplets generated and/or a droplet count. The terms manipulating and controlling are used interchangeably herein.

The present invention also provides feedback control system for assessing and manipulating a predetermined characteristic of a microfluidic droplet including: (a) providing a microfluidic system comprising at least one microfluidic channel containing at least one fluidic droplet; (b) acquiring a plurality of images of the fluidic droplet at a plurality of time points within the microfluidic channel, wherein the plurality of images comprises an image set; (c) assessing the predetermined characteristic of the fluidic droplet in the microfluidic channel using an image sensor; and (d) transmitting the assessment from the image sensor to a feedback controller, wherein the feedback controller adjusts a flow rate of one or more fluids, thereby manipulating the predetermined characteristic of the fluidic droplet within the microfluidic channel. The system can further include: assessing said predetermined characteristic of said fluidic droplet in said microfluidic channel, within each image set, using an image sensor; comparing said assessment of said predetermined characteristic of said fluidic droplet in each image set; and determining an average assessment of said predetermined characteristic of said fluidic droplet; wherein said feedback controller adjusts a flow rate of one or more fluids, thereby increasing the accuracy of the assessment.

Microdroplets are essentially miniaturized test tubes with a volume of less than 1 pico-liter (one trillionth of a liter) to several hundred nanoliters (one billionth of a liter). Because of their incredibly small size, each microdroplet requires only a very small amount of sample to conduct chemical reactions, biological assays and medical testing, thus yielding a wealth of information for biomedical and chemical studies from very limited source material at relatively low cost, e.g., a 10 microliter sample can be used for 1 million reactions with each reaction using 10 pico-liters. Furthermore, microdroplets can be introduced into microfluidic devices, which feature a series of micrometer-sized channels etched or molded into a chip where microdroplets can be manipulated by directing the flow of the fluids that carry them. The term "carrier fluid" or "carrier fluids" refers to any fluid which contains droplets and transports them through microfluidic channels of microfluidic devices. Carrier fluids are described in greater detail herein.

In microfluidic devices, microdroplets can be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays. Although major improvements in regulating droplet size and uniformity, and modifying droplet surface chemistry have been achieved, the utility of microdroplets in chemistry, biology, and medicine depends critically on the spatiotemporally precise delivery of microdroplets of various properties through the channels in microfluidic devices.

In order to utilize microdroplets for rapid large-scale chemical screening or complex biological library identification, different species of microdroplets, each containing the specific chemical compounds or biological probes of interest, have to be generated and combined at the preferred conditions, e.g., mixing ratio and order of combination. For example, one microdroplet of species A must be combined with one microdroplet of species B, but not with two microdroplets of species B or with one microdroplet of species C. The ratio of combining different species of microdroplets is achieved by adjusting the frequencies at which microdroplets are delivered to the site of combination. The terms "frequency" or "frequencies" refer to the rate at which microdroplets of certain species are delivered to a specific location. Moreover, this frequency or rate is a number per unit time, typically several hundred to tens of thousands per second. Furthermore the terms "frequency" or "frequencies" refers to the number of times at which droplets of certain species are delivered to a specific location. The location can be where certain behaviors of droplets (e.g., pairing, merging, combination, etc.) occur or where certain actions (e.g., electrification, mechanical deformation, etc.) are applied to droplets. Preferably, the location is where combination of droplets occurs.

Preferably, each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. In the merge zone, droplets are induced to coalesce into a single droplet, preferably an electric field is utilized to induce coalescence. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. Feedback on the infusion rates of the carrier fluid and the dispersed fluid provides droplets that are uniform in size and generated at a fixed frequency over arbitrarily long periods of time. However, sample to sample variations in viscosity, viscoelasticity, surface tension or other physical properties of the sample fluid coming from but not limited to the inclusion of polymers, detergents, proteins, cells, nucleic acids or buffering solutions, influence the droplet size, and, hence, frequency of generation in an unpredictable way, generating a significant problem to be solved. Hence, the same nozzle on the same substrate with same carrier fluid, but a different dispersed fluid will result in a different droplet volume at a different frequency. Moreover, often it is desirable for one of the species introduced at the confluence to be a pre-made library of droplets where the library contains a plurality of reaction conditions, e.g., a library can contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into a inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets can be reliably matched at a confluence by simply using fixed infusion rates. In addition, these limitations also have an impact on the extent to which volumes can be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

As a result of the above factors, current microdroplet technologies cannot efficiently or reliably be used for applications involving combining droplets of different species at high frequencies. Consequently, there is a need in the art for novel methods of manipulating droplet frequency of generation, frequency of library droplet introduction and droplet volume.

It is well established to one of ordinary skill in the art that objects and geometrical properties of objects are identified from standard image acquisition and machine vision protocols. For example, objects in images of microfluidic channels such as droplets, channel walls, or contaminating particulate are readily distinguished and classified by their boundary, projected area, and ellipticity of the objects.

The invention provides a method for capturing images of objects within microfluidic channels such as microdroplets and channel walls, collecting the information to measure and assess both frequency and volume, and subsequently changing the infusion rates to match specific set points. The benefit of using image processing to measure droplet parameters in-situ allows system requirements such as pump flow rate accuracy and microfluidic channel tolerances to be relaxed. Thus, image processing protocols provide the practical advantage of reducing the system cost.

The invention provides a feedback control system for microfluidic droplet manipulation of one or more predetermined properties or characteristics of a microdroplet. One embodiment of the invention is directed to a system for dynamically measuring or assessing, and controlling or manipulating droplets via machine vision for feedback measurement and adjusting fluid flow rates to manipulate one or more predetermined properties or characteristics of a microdroplet. Examples of controllable droplet properties or characteristics include, but are not limited to, droplet volume, droplet generation rate, droplet release rate, and the total number of droplets generated. Preferably the selective manipulation occurs with droplets in a microfluidic device. Such microfluidic devices are generally known in the art. Exemplary preferred microfluidic devices are provided by U.S. Publication No. US 2008/0003142, International Publication No. WO 2008/063227, U.S. Publication No. US 2008/0014589, and International Publication No. WO 2007/081385, each of which are incorporated herein by reference in their entirety. Flow rates are adjusted by a drive infusion system that is not constrained to a defined technology or mechanism. Methods of the invention encompass art-recognized drive infusion systems, including those systems disclosed in U.S. Publication No. US 2008/0003142, International Publication No. WO 2008/063227, U.S. Publication No. US 2008/0014589, and International Publication No. WO 2007/081385. Furthermore, exemplary drive infusion systems of the methods of the invention include, but are not limited to, a syringe pump, pressure head, electrokinetic drive or any other means known in the art.

Figure 3:
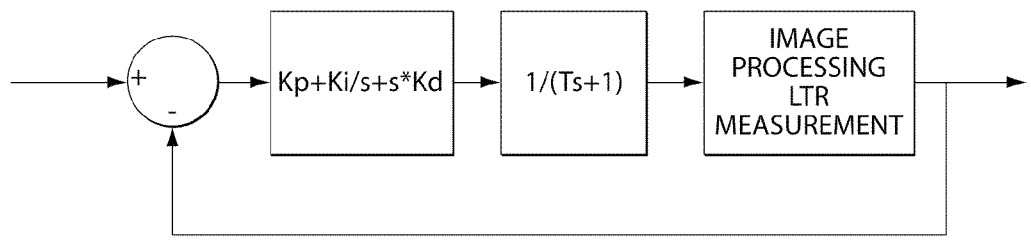
FIG. 3 is a schematic diagram of "feedback control," in which system inputs are adjusted according to measured system outputs.

"Feedback control," as shown in FIG. 3, refers to adjusting system inputs according to measured, assessed, characterized, or determined system outputs. Exemplary system outputs include, but are not limited to, the image processing LTR measurement, an assessment from an image scanner (a measurement of size, speed, frequency, refractive index, extinction coefficient, color, volume, area, number, phase, coalescence, or a determination of the contents of a microfluidic droplet), a characteristic or property of a microfluidic droplet or plurality of droplets (size, speed, frequency, refractive index, extinction coefficient, color, volume, area, number, phase, coalescence, content or activity thereof, fluorescence, or any change thereof), a characteristic or property of a fluid within a microfluidic channel (content, viscosity, surface tension, clarity, opacity, thickness, shear forces, speed, volume, pressure, temperature, and solubility), and a characteristic or property of the microfluidic device itself. Exemplary system inputs include, but are not limited to, a microfluidic droplet or a plurality of microfluidic droplets, one or more fluids, automated instructions transmitted to one or more pumps or devices that control a fluid within a microfluidic device, or automated instructions transmitted to one or more pumps or devices that control to introduction of droplets into a microfluidic channel or the production, generation, or creation of a microfluidic droplet within a microfluidic channel of a microfluidic device. System outputs are assessed, and signals or instructions are transmitted from a feedback controller to a device that controls a system input. The feedback controller adjusts system input either in response to changing system outputs to maintain a constant state of efficiency or to manipulate a microfluidic droplet or plurality of droplets.

The present invention provides methods to selectively measure or assess and manipulate the absolute or relative droplet volume. The relative droplet volume can be determined by analysis of an image captured by an image scanner. This analysis includes capturing an image of a droplet, or a plurality of droplets, at a point in a microfluidic channel containing a lithographically inscribed size marker, such as a circle or a square; determining the number of image pixels occupied by a droplet and by the size marker; and comparing the resultant pixel numbers to determine a relative droplet volume. Absolute droplet volume is determined by dividing a flow rate, such as the infusion flow rate, represented as Q, by the droplet frequency, represented by ν, in the following equation:

$$\overline{V} = \frac{Q}{\nu}.$$

In one example, the droplet volume is controlled by adjusting the drive fluid through feedback control based on the droplet projected area as measured by an image sensor. In a preferred embodiment of this method, the image sensor is a digital image sensor. In another example, the droplet volume is controlled by adjusting the drive fluid through feedback control based upon the droplet volume, as measured or assessed by Pulsed Illumination Scanning (PILS).

The present invention also provides methods to selectively manipulate droplet pairing ratios. The present invention provides a feedback control system for manipulating microfluidic droplet pairing ratios including: (a) providing a microfluidic system comprising at least one microfluidic channel; (b) introducing a first plurality of fluidic droplets within the microfluidic channel at a first frequency; (c) introducing a second plurality of fluidic droplets within the microfluidic channel at a second frequency, wherein at least one fluidic droplet from the first plurality and at least one fluidic droplet from the second plurality are paired; (d) assessing the first frequency and the second frequency using an image sensor; and (e) transmitting the assessment of the first and the second frequency from the image sensor to a feedback controller; wherein the feedback controller adjusts a flow rate of one or more fluids to maintain the first and the second frequency at the same frequency, thereby manipulating the pairing ratios of the first and second pluralities of fluidic droplets within the microfluidic channel. The present invention also provides a feedback control system for manipulating microfluidic droplet pairing ratios including: (a) providing a microfluidic system comprising at least one microfluidic channel; (b) introducing a first plurality of fluidic droplets within the microfluidic channel at a first frequency; (c) introducing a second plurality of fluidic droplets within the microfluidic channel at a second frequency; (d) assessing the first frequency and the second frequency using an image sensor; and (e) transmitting the assessment of the first and the second frequency from the image sensor to a feedback controller; wherein the feedback controller adjusts a flow rate of one or more fluids to provide a desired frequency ratio of the first to the second plurality of droplets, thereby manipulating the pairing ratios of the first and second pluralities of fluidic droplets within the microfluidic channel.

The frequencies of a first droplet and a second droplet, or a first plurality and a second plurality of droplets, are controlled relative to each other to have the same frequency but out of phase such that the droplets are intercalated, or interdigitated, (and thus paired) when traveling through the microfluidic channel. A first plurality of droplets and a second plurality of droplets having identical or matched frequencies, and which enter a microfluidic channel at the same time, are out-of-phase when either the first or second plurality of droplets travel down the microfluidic channel at a different speed from the other. As such, the droplets of the first and second pluralities intercalate, or interdigitate, because they do not travel together. In a preferred embodiment, the frequencies of the first and second pluralities are not identical, but rather matched, such that intercalation, or interdigitation, of the droplets still occurs. For example, the frequency of a second plurality of droplets that is matched to the frequency of a first plurality of droplets is greater to or less than the frequency of the first plurality by approximately 1, 10, 100, or 1000 Hz, or any point in between.

The present invention further provides methods to selectively manipulate the number of droplets generated. In one example, the system counts the number of droplets generated and stops pump flow once the desired number of droplets is reached. Thus, the present invention provides a feedback control system for controlling microfluidic droplet count including: (a) providing a microfluidic system comprising at least one microfluidic channel; (b) introducing at least a first plurality of fluidic droplets within the microfluidic channel at a first frequency; (c) assessing the first frequency using an image sensor; (d) determining the time required to produce a predetermined amount of fluidic droplets based upon the frequency assessment; and (e) transmitting the assessment to a feedback controller, wherein the feedback controller stops the introduction of the droplets after the determined time, thereby controlling the microfluidic droplet count.

The present invention provides a process including droplet detection, droplet assessment and characterization, and feedback control, for selectively manipulating the various droplet properties or characteristics in a microfluidic device.

Machine vision provides a means to accurately detect and characterize properties of droplets. Droplet characterization is then used to adjust the fluidic system inputs, fluid flow rates and drive infusion flow rates to manipulate the droplet characteristics or properties. These characterization and control schemes are applied in parallel, for example frequency, droplet diameter and droplet pairing are controlled at the same time. Alternatively, these characterization and control schemes are applied in series, for example frequency, droplet diameter and droplet pairing are controlled sequentially.

The invention provides a method for measuring and controlling the arrival frequency of regularly separated objects, e.g. droplets, including the measurement of multiple images acquired at different times (e.g. image sets) to measure the displacement of the objects, and acquisition of different image sets at varying times between images to reduce the uncertainty in the measurement. Methods of the invention accurately and inexpensively measure droplet frequency and volume. The present invention provides methods to selectively manipulate the frequency of droplets generated and released by adjusting the flow rate of a fluid, for example, the carrier fluid or drive fluid. In one example, the flow rate of the carrier fluid and drive fluid is adjusted in response to detecting the distance a single droplet moves during a known quantity of time, e.g. as determined by Pulsed Illumination Scanning "Droplet pairing" refers to the process of interleaving different classes of droplets at a time variant ratio (e.g. user settable function or constant value). The ratio is defined as x droplets of species A for every droplet of species B. In one example, two different classes of droplets are intercalated, or interdigitated, wherein the droplets differ in size (e.g., diameter, perimeter, diagonal, volume, area of cross-section etc), shape (e.g., spherical, elliptical, rectangular, etc.), color, refractive index or extinction coefficient. The term "refractive index" refers to the ability of a medium (e.g., glass, air, solution, etc.) to reduce the speed of waves (e.g., light, radio wave, sound wave, etc.) traveling inside the medium. The term "extinction coefficient" refers to the strength of a medium (e.g., glass, air, solution, etc.) to absorb or scatter light. The term "cross-section" refers to the intersection of a body in 2-dimensional space with a line, or of a body in 3-dimensional space with a plane. Preferably, cross-section refers to the intersection of a body in 3-dimensional space with a plane.

In a further example, the two classes of droplets have different diameters. All droplets in the microfluidic device within the ROI are detected using the previously specified droplet detection algorithm. The droplets are further classified as species A or species B depending on the droplet area. The droplet pairing ratio is measured by counting the number of species A droplets that are found upstream of each species B droplet. Species A has a smaller droplet diameter and travels faster than species B. Only the upstream Species A droplets will merge with downstream Species B droplets due to the differences in velocity. The species A droplets corresponding to a species B droplet at the inlet of the microfluidic channel are not counted in the droplet pairing measurement as it is not possible to detect and classify the off image-frame upstream droplet to get an exact pairing ratio for that species A: species B droplet set.

Figure 4:
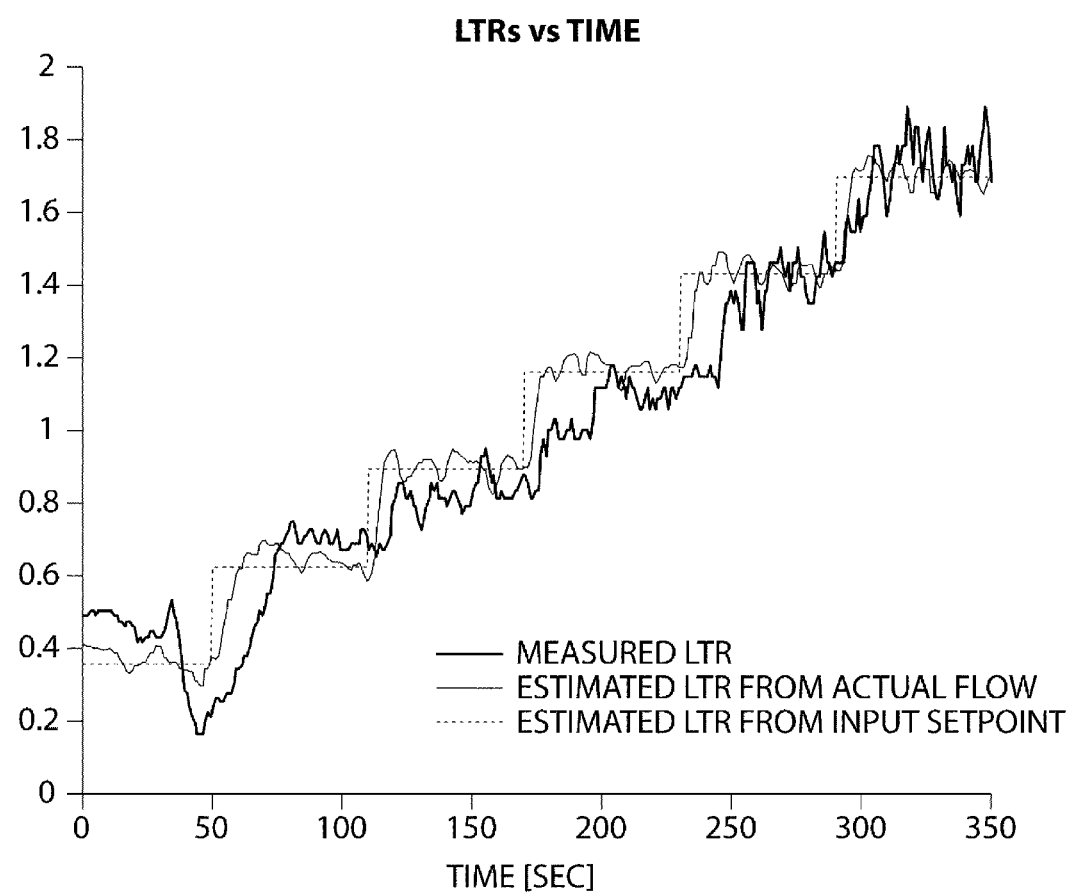
FIG. 4 is a graph of the Library to Template Ratio (LTR), also referred to as the droplet pairing ratio, versus time, showing that the droplet pairing ratio is well controlled over a range from 0.4 to 1.75 by adjusting the carrier fluid flow rates.
Figure 5A:
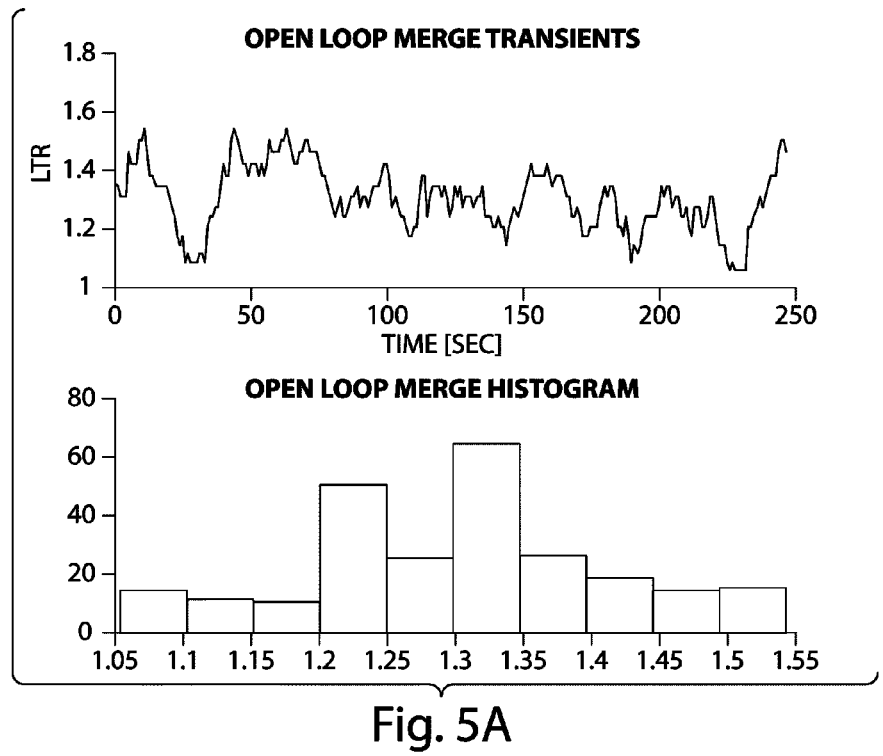
FIG. 5A is a pair of graphs, a line graph and its corresponding histogram, of the relationship of the LTR for open loop operation (with a rather large CV of 8.5%) versus time, showing that the output, or LTR, is not centered about the set point of 1.
Figure 5B:
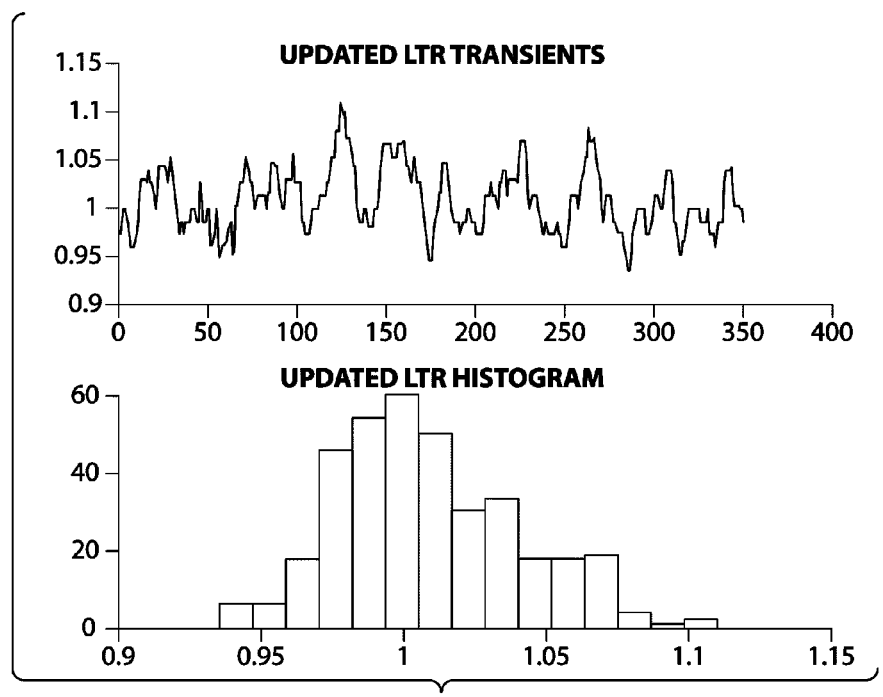
FIG. 5B is a pair of graphs, a line graph and its corresponding histogram, of the relationship of LTR for closed loop feedback (with a CV of 3.0%) versus time, showing that the output, or LTR, is centered about the set point of 1.

As shown in FIG. 4, the droplet pairing ratio (also referred to as Library to Template Ratio [LTR]) is well controlled over a range from 0.4 to 1.75 by adjusting the carrier fluid flow rates. FIG. 5a shows the LTR for open loop operation with a rather large CV (Coefficient of Variation (i.e., Standard Deviation/Mean)) of 8.5% and isn't centered about the set point of 1. FIG. 5b shows the results of applying closed loop feedback on the LTR, the output is centered on the set point of 1 and has a CV of 3%.

The invention provides a f feedback control system for independently controlling microfluidic droplet volume and frequency comprising: (a) providing a microfluidic system comprising at least one microfluidic channel; (b) producing a plurality of fluidic droplets within a carrier fluid within said microfluidic channel using a drive fluid; (c) assessing the frequency, volume, and flow rate of said plurality of droplets using an image sensor; (d) transmitting said assessed frequencies, volumes, and flow rates of the plurality of droplets from said image sensor to a feedback controller; (e) adjusting a flow rate of the carrier fluid using said feedback controller to attain a predetermined droplet frequency set point; and (f) adjusting a flow rate of the drive fluid using said feedback controller to attain a predetermined droplet volume set point; wherein said feedback control system independently determines and controls microfluidic droplet frequency and volume.

Droplet volume and frequency are intrinsically linked through the law of mass conservation; droplet frequency multiplied by droplet volume is the droplet volumetric flow rate. Neglecting any system losses such as leaks, the droplet volumetric flow rate is determined by the drive pump flow rate. The droplet frequency is a function of many factors such as the microfluidic nozzle geometry, carrier fluid flow rate, fluidic shear forces, viscosity, and surface tension and will thusly be different for different fluids even when operating under the same pump flow rates. Typically the fluidic system will be initialized with empirically found pump flow rates starting the system near the desired frequency rate and droplet volume set point. The first stage of control then starts to adjust the carrier-pump flow rate to move the droplet frequency towards the desired set point. Droplet frequency and volume are highly non-linear as a function of carrier flow rate, but in general, increasing the carrier flow rate will increase the droplet frequency and decrease droplet volume. Decreasing the carrier flow rate decreases the droplet frequency and increases the droplet volume. Once the droplet frequency has settled the second stage of control then adjusts the flow rate to manipulate the droplet volume towards the desired set point. Preferably, the second stage of control adjusts the drive pump flow rate and the resultant drive fluid.

The measurement of absolute droplet volume is of fundamental importance, but traditional methods of measurement require specialized skills in the art and relatively expensive optical instruments. These methods include fluorescence burst analysis and image analysis of projected droplet area, where the latter requires independent calibration most often achieved by the former method. Methods of the invention are easy to use, amenable to automation, and inexpensive to implement. This method can be used in conjunction with the imaging-based control feedback described above to create steady streams of droplets of known absolute size and frequency. The traditional methods are described first, below.

The most accessible measurement related to droplet volume is the volumetric flow rate, Q, of the sample fluid, that is, the liquid phase that forms the droplets and as opposed to the carrier fluid that surrounds the droplets. Typical microfluidic flow rates between 10 to $10^4$ μL/hr can be measured by numerous methods including piston displacement and heat transfer. Thus, all that remains to determine the average droplet volume is to measure the droplet frequency, v, because the average droplet volume, $\overline{V}$, equals $$\overline{V} = \frac{Q}{v}.$$

This commonly used relationship yields an average droplet size because the droplet frequency is determined over an ensemble of droplets.

Droplet frequency poses a more significant measurement challenge. Frequencies often reach ~10 kHz, requiring a measurement system with a very fast time response. Laser-induced fluorescence is the most common method, taking advantage of the high speed of low light detectors such as PMTs. In this method, droplets containing fluorophores emit a steady train of fluorescence bursts that is readily translated into droplet frequency by standard Fourier analysis. While quite robust, this approach requires familiarity with laser alignment inside a microscope and it also requires both expensive fluorescence excitation and detection. Methods of the invention eliminate both of these requirements.

The invention provides a method called Pulsed Illumination Scanning (PILS). The PILS method is a variant of conventional particle image velocimetry (PIV) that has been optimized for steady streams of regularly spaced droplets. Both approaches measure velocity by monitoring particle/droplet displacement in between successive images separated by a delay time, $\Delta T$. As an example, in PIV the cross-correlation of two successive images of a field of randomly dispersed particles yields a singular peak corresponding to the uniform displacement of all of the particles in the field of view. However, cross-correlation of successive images of regularly spaced droplets yields a repeating set of peaks because each individual image has a high degree of autocorrelation. That is, except at the shortest delays between images, it is very difficult to deduce a priori which droplets correspond to each other. At very short delays, the percent uncertainty in the displacement measurement is unacceptably high for most applications.

In the PILS method, pairs of successive images are recorded with an increasing delay in time between images (increasing $\Delta T$). The initial $\Delta T$ must be significantly shorter than the droplet period (the time between droplet arrivals, or 1/v) to avoid ambiguity in droplet associations between images. $\Delta T$ is then increased gradually to reduce the percent error in the displacement measurement, but without losing track of droplet associations. In fact, $\Delta T$ can even significantly exceed the droplet period so long as the association is maintained. In this manner, the PILS method overcomes the shortcomings of PIV by using both short delays to establish associations and long delays to reduce experimental error. However, manually stepping between delays can be quite tedious, so a specific PILS method based on Fourier analysis, called fPILS is provided herein. fPILS is readily automated.

Figure 9A:
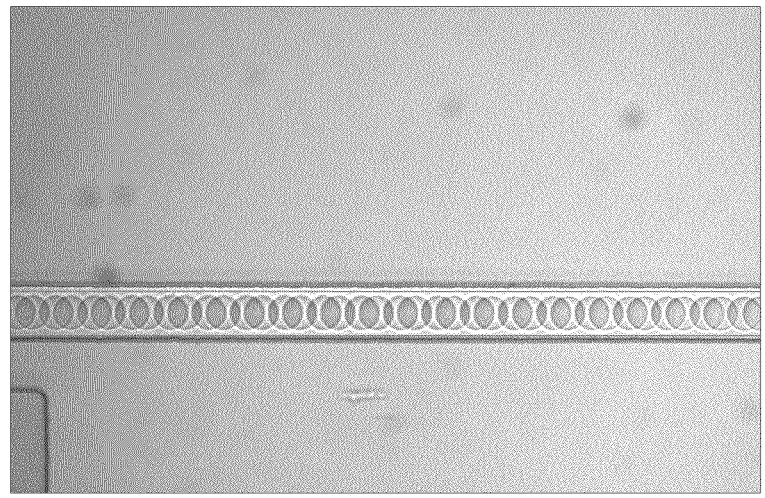
FIG. 9A a line-cut along the droplet train of a microfluidic channel.
Figure 9B:
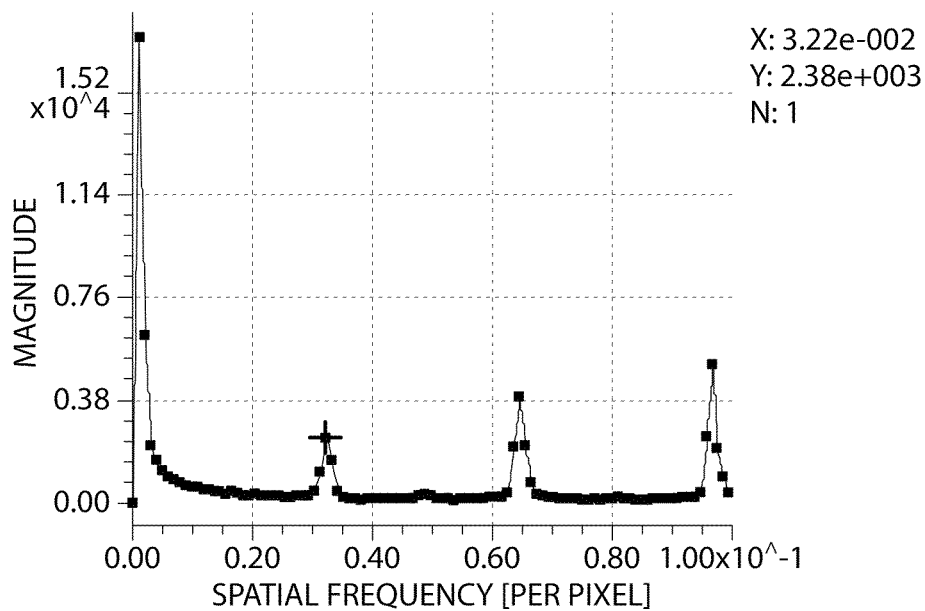
FIG. 9B is a one-dimensional Fourier transform of a line-cut along the droplet train (line cut in FIG. 9A) revealing the fundamental droplet frequency (spatial frequency) and its higher order harmonics.
Figure 9C:
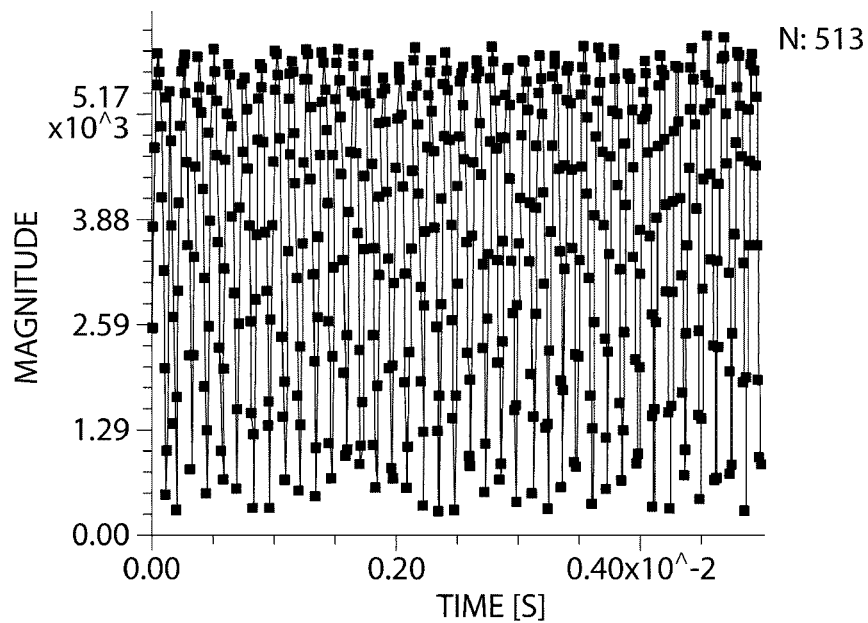
FIG. 9C is the amplitude of the fundamental frequency after each increase in the change in time, ΔT in multiple illumination images.
Figure 9D:
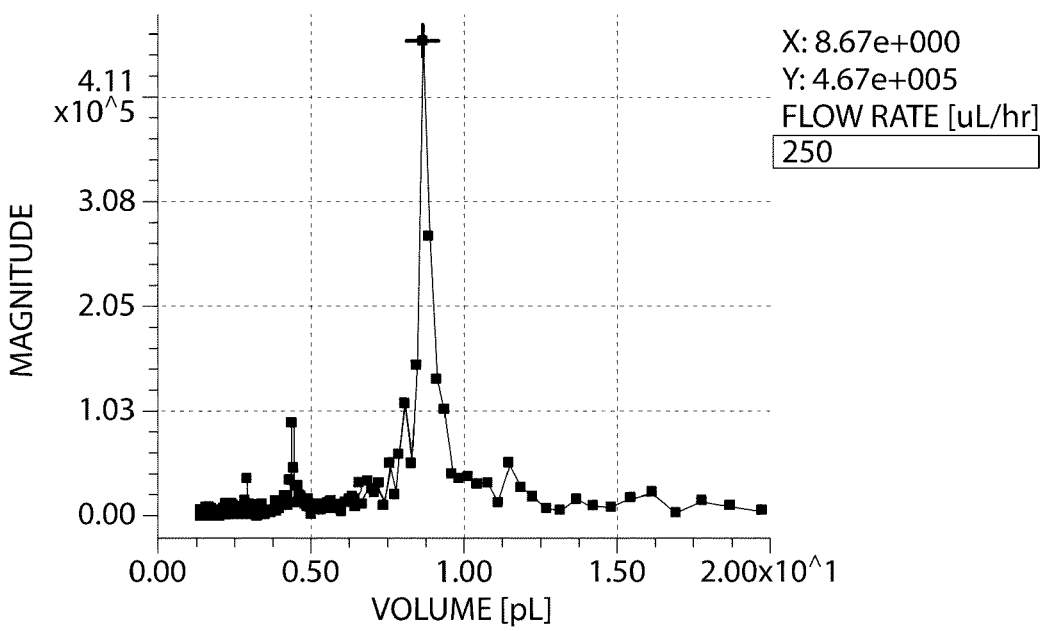
FIG. 9D is a second Fourier transform of the dependence of the fundamental frequency on ΔT revealing the desired temporal frequency of the droplets as a single pronounced peak.

In the first step of the fPILS method, a one-dimensional Fourier transform of a line-cut along the droplet train (line cut in FIG. 9A) reveals the fundamental droplet frequency (spatial frequency) and its higher order harmonics (FIG. 9B). The fundamental spatial frequency can be identified from a single image, but subsequent analysis requires both images separated by $\Delta T$ to be superimposed. A convenient and inexpensive method of superimposing images used here employs short pulses of illumination from an LED and an extended camera exposure that catches both pulses. The amplitude of the fundamental frequency is then monitored after each increase in $\Delta T$ (FIG. 9C) in the multiple illumination images. The amplitude of the fundamental spatial frequency oscillates with a period equal to the droplet period. This can be understood by considering the case when $\Delta T$ equals half the droplet period. In this case, the droplets in the second exposure appear halfway in between the droplets from the first exposure. In effect, the superimposed image looks like the droplets have exactly doubled their frequency. The new fundamental spatial frequency is now twice the original, and the amplitude of the original frequency is ideally zero. Thus the amplitude of the fundamental spatial frequency oscillates between a maximum at overlap of droplets and a minimum at ½ offset between droplets with a period equal to the droplet period. A second Fourier transform of the dependence of the fundamental frequency on $\Delta T$ reveals the desired temporal frequency of the droplets as a single pronounced peak (FIG. 9D).

The fPILS method is low cost, robust, precise, and accurate. The method only requires an inexpensive camera that is standard equipment on any droplet characterization platform, a very inexpensive LED, and a simple pulsed current source to power the LED. The LED pulser used here was based on the common and inexpensive PIC microcontroller. The method is also extremely robust against drift in microscope focus because it is based on the repetition of features within an image. Even quite out-of-focus images show excellent repetition. The resolution of the measurement rivals alternative approaches when many periods of the oscillation in fundamental spatial frequency are observed. In fact, at the longest $\Delta T$'s in FIG. 9C the droplets in the first image have completely displaced outside of the field of view in the second image. Such extended $\Delta T$'s are impossible with conventional PIV, highlighting the extra information accessible from a repetitive system. The accuracy of the method is dependent on the uncertainty in $\Delta T$ and Q. Typically $\Delta T$ is very well known, originating from an extremely accurate and precise crystal oscillator. Thus, the overall uncertainly in the measurement is most likely dominated by the error in Q.

Figure 6:
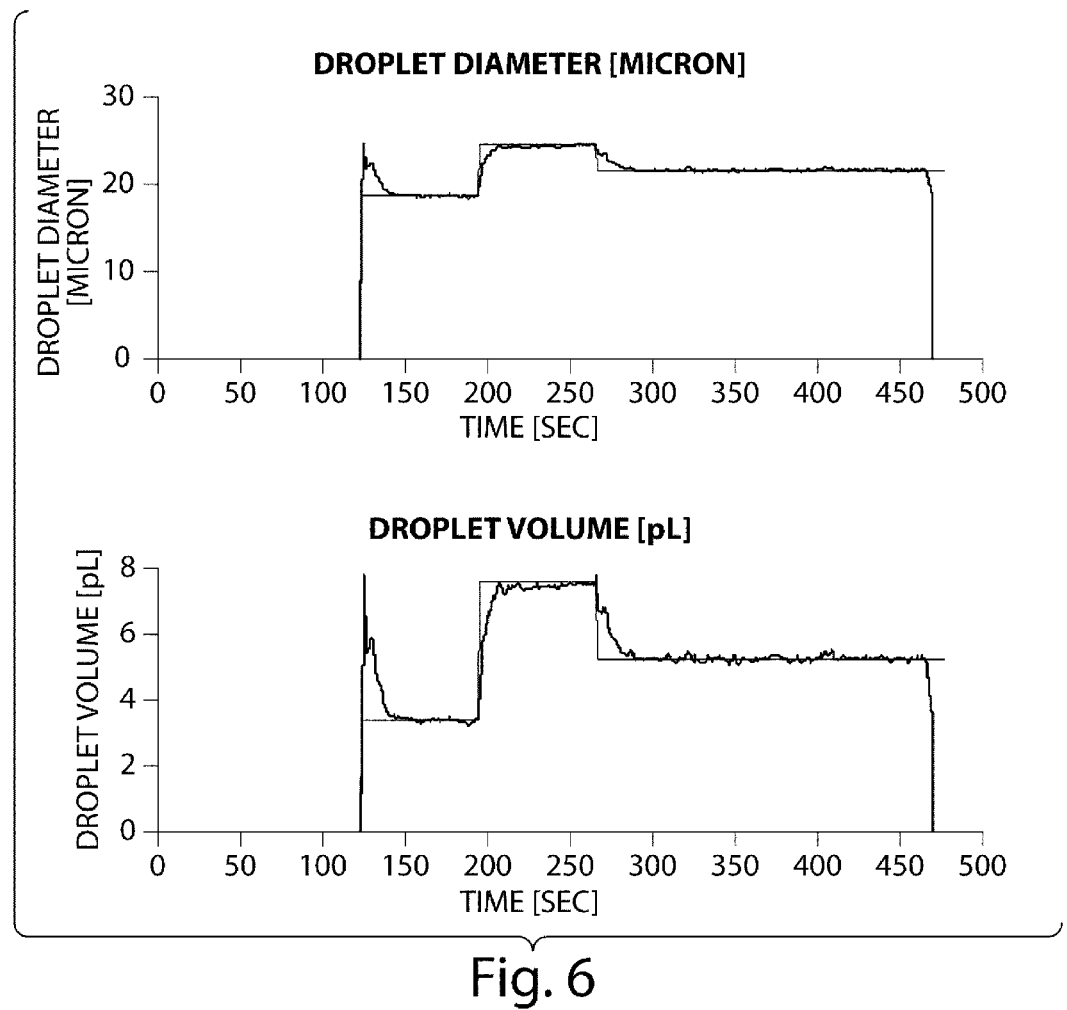
FIG. 6 is a pair of graphs of droplet diameter (top) or droplet volume (bottom) versus time, demonstrating the droplet volume control step response. Green or Straight Line=set point. Blue or Jagged Line=measured output.
Figure 7:
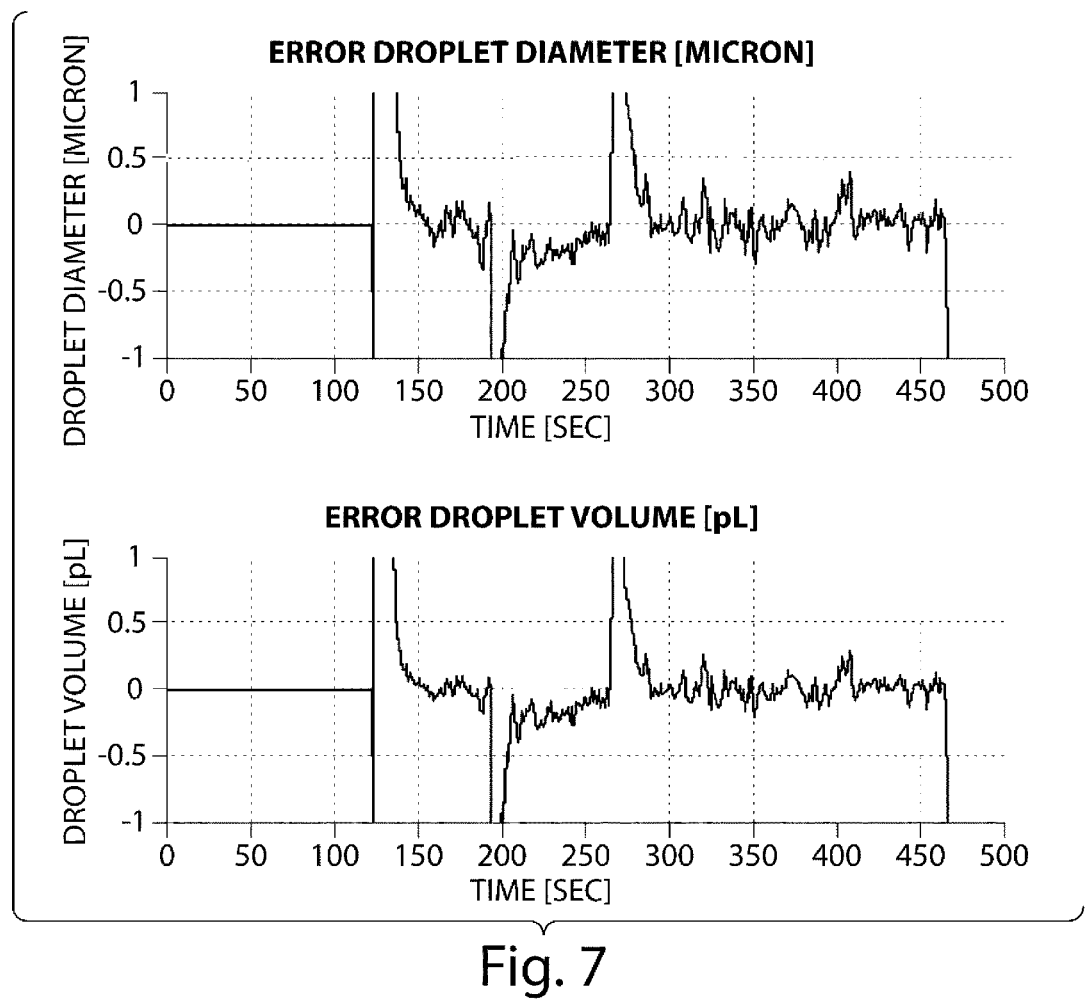
FIG. 7 is a pair of graphs of droplet diameter (top) or droplet volume (bottom) versus time, demonstrating that error in the droplet volume is minimal, i.e. below 0.5 pL.

An example of droplet volume control is shown in FIG. 6. The droplet volume is detected using either fPILS or inferred from the droplet projected area as detailed in the droplet detection section. The drive fluid is then automatically adjusted using PID control to control the droplet volume. It can be seen that droplet diameter and droplet volume are quite controllable and settle to the desired set point in under 20 seconds. FIG. 7 shows the error in the droplet volume is quite low, well below 0.5 pL.

Similarly to droplet volume control, above, the droplet frequency can be controlled in a straightforward manner. The droplet frequency can be measured directly by the fPILS method, fluorescence burst analysis, or any other method. Comparison of the measured frequency with the target set point yields an error signal that can be fed back to a standard controller, such as a PID controller. In the preferred control scheme, the carrier flow rate is increased to increase the droplet frequency, and vice versa. Any other method of adjusting the droplet frequency can also be used.

Figure 8:
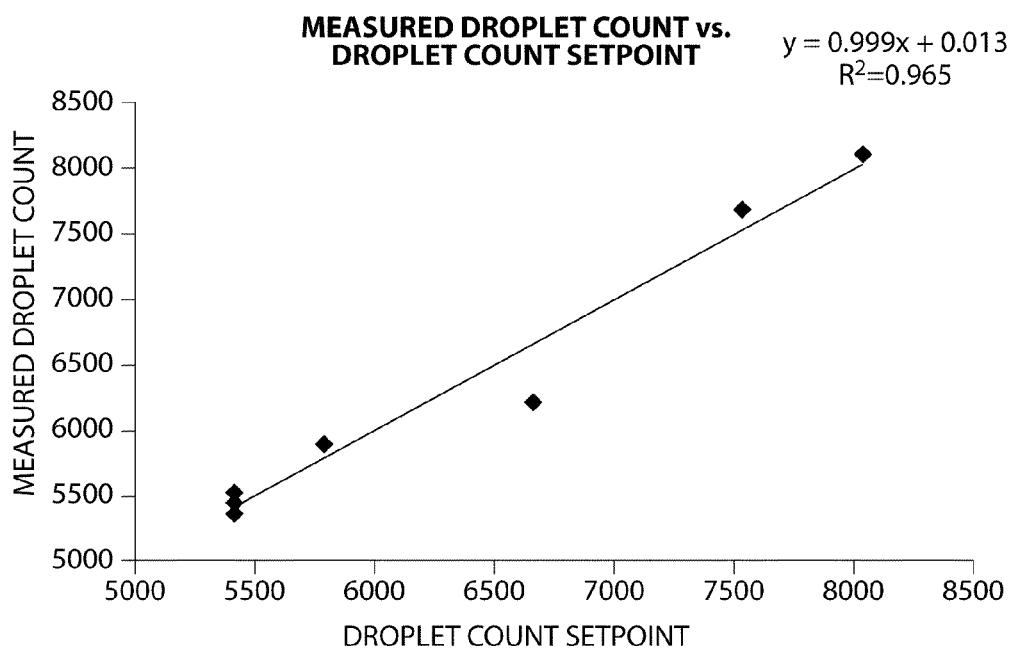
FIG. 8 is a graph of the measured droplet count vs. droplet count set point, demonstrating droplet count control.

An example of droplet count control is shown in FIG. 8. The current total droplet count is detected by integrating the fPILS algorithm output over time or by integrating the droplet count per image frame over time. Once the desired number of droplets has been detected, all plump flow stops, thus stopping droplet formation/release. It can be seen that the droplet release/generation count is quite controllable over a large range and is highly linear.

This present invention provides various methods of droplet detection and analysis.

"Droplet detection" refers to the identification and selection of droplets through an automatic process. In one example, droplet detection includes the steps of image acquisition, intensity thresholding, area thresholding, circularity filtering and accumulating the filtered results. The term "image acquisition" refers to acquiring images of droplets. In a preferred aspect of this method, images of droplets are acquired in a microfluidic device. In another preferred aspect of this method, images of droplets are acquired in the region of interest (ROI). As used herein, "region of interest" or "ROI" refers to locations in the microfluidic device where certain behaviors of droplets (e.g., pairing, merging, combination, etc.) occur or where certain actions (e.g., electrification, mechanical deformation, etc.) are applied to droplets. Preferably, the region of interest or ROI has two ends wherein one end is at the location where droplets enter the ROI and the other end is at the location where droplets exit the ROI. In a preferred example, the ROI is where pairing of droplets occurs. In another preferred example, the ROI is where combination of droplets occurs.

Image acquisition is performed using a device with means to capture images at a sufficient acquisition rate (e.g., 10 images per second) and exposure time (between 1-10 µs, preferably 5 µs). Alternatively, or in addition, images are acquired with a digital device (e.g., digital camera). The composition of the droplets has a different refractive index from that of the surrounding carrier fluid. Thus, due to refraction, the boundary of the droplet has a different brightness, e.g., the boundary of the droplet is darker. Therefore, the corresponding pixels in the image have different values from those of the surrounding pixels.

One method of droplet detection is machine vision. One of ordinary skill in the art of machine vision knows that each image must have sufficient contrast, focus and resolution to have a robust detection method. Thus, adjusting the optics, illumination and focus to obtain a suitable image is imperative for droplet detection. The term "accumulated contour detection" refers to the process in which droplets are detected and characterized through multiple image processing filters as follows:

1. "Intensity threshold" the image at threshold t. In one example t is initialized to the minimum image intensity value.
2. Detect all contours in the threshold image ("contour detection").
3. Filter contours based on "area thresholding."
4. Filter contours based on "circularity thresholding."
5. Filter contours based on spatial location within the image.
6. Accumulate contours into the "contour accumulator image." For example, in FIG. 1, an image of droplets in the ROI shows droplets of two sizes (top panel). The bottom panel shows the final "contour accumulator image" where grey level intensity corresponds to the number of times each pixel was added to the accumulator image. All other pixels were assigned the value "0", shown as black.
7. Increment the threshold value t.
8. Repeat steps 1 though 7 until t reaches the maximum image intensity value.
9. "Intensity threshold" the "contour accumulator image" to select only droplets with a significant number of votes.

The term "intensity thresholding" refers to the process where the value of each pixel in an image is compared with a preset value called "threshold value", and pixels that have a value lower than the threshold value are assigned a designated value, e.g., 0, and pixels that have a higher value are assigned another designated value, e.g., 1. The output is called a binary threshold image.

The term "contour detection" refers to the process where the perimeter of connected non-zero pixels is detected. Connectivity defines which pixels are connected to other pixels. A set of pixels in a binary threshold image that form a connected group is referred to as an "object" and the perimeter of the "object" is referred to as a "contour".

The term "area thresholding" refers to the process where the number of pixels in an area confined by a "contour" is calculated and compared with a set of preset values, and, according to the result from the comparison, all pixels included in the area are assigned to designated values, e.g., 0 and 1. In one example, areas with the number of pixels either smaller than a preset value $t_1$ or bigger than a preset value $t_2$ are assigned a designated value, e.g., 0, to all their pixels, and areas with the number of pixels no smaller than $t_1$ and no bigger than $t_2$ are assigned a designated value, e.g., 1, to all their pixels. Area thresholding detects droplets of sizes within a given range The term "circularity filtering" refers to the process where formula I is applied to an area confined by a contour and the resulting value Circ is compared with a preset range of values. Only those areas with a Circ value within the given range are selected. For droplets that are spherical, and, thus, have a circular cross-section, circularity filtering removes contaminants which often have irregular shapes. In formula I, Area and perimeter refer to the total number of pixels included in the area and the total number of pixels present on the boundary of the area, respectively.

$$Circ = \frac{4\pi \cdot Area}{perimeter^2} \tag{I}$$

The term "contour accumulation" refers to the process where the results of intensity thresholding, contour detection, area thresholding and circularity filtering are summed into an "accumulator image". The "accumulator image" keeps count of the number of times each pixel passes the applied filters. Only pixels that pass the filters many times are actually droplets; this reduces spurious results from illumination variations and digital sensor noise.

Figure 2:
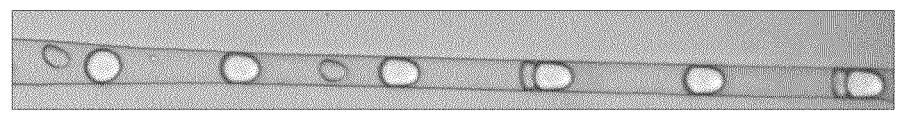
FIG. 2 is a photograph of an image of microdroplets shown in cross-section, in which the droplets of bigger cross-sectional area were pseudo-colored yellow (light shaded droplets) and the droplets of smaller cross-sectional area were pseudo-colored blue (dark shaded droplets).

The term "Droplet classification" refers to the process where droplets are classified according to their specific properties. Such properties include, but are not limited to, size (e.g., diameter, perimeter, diagonal, volume, area of cross-section, moments of inertia, etc.), shape (e.g., spherical, elliptical, rectangular, etc.), color, refractive index and extinction coefficient. In one example, the droplets are classified according to the area of their cross-section. For example, in FIG. 2, cross-sections of droplets are shown, and the droplets of bigger cross-section area were automatically colored yellow (light shaded) and the droplets of smaller cross-section area were colored blue (dark shaded).

Figure 10:
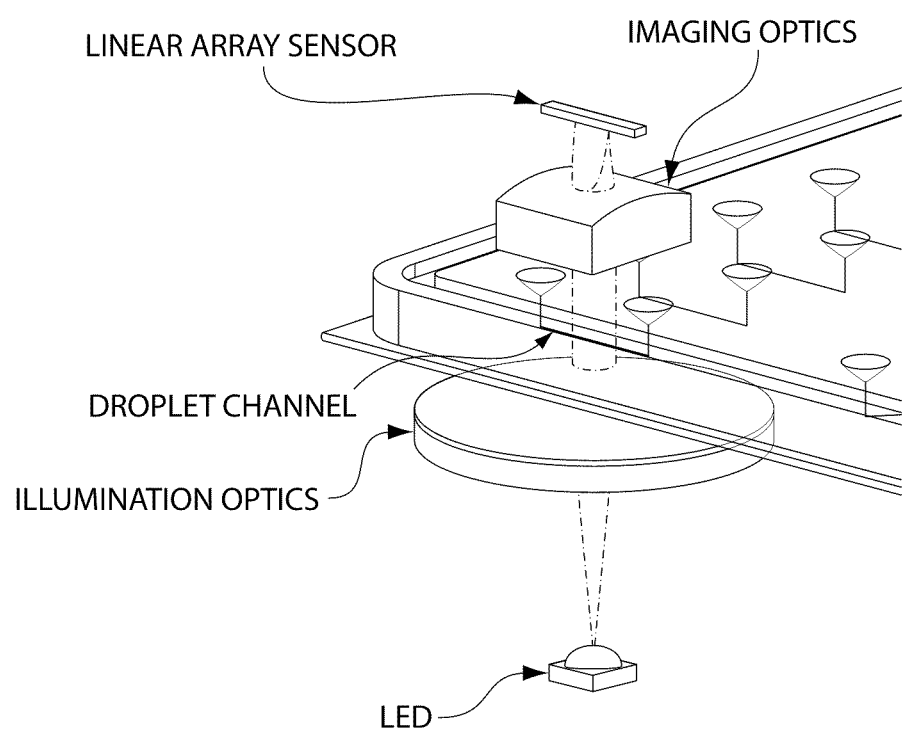
FIG. 10 is an illustration of a trans-illumination scheme.

The invention provides a method to measure every single droplet at nominal generation rates (typically 1 kHz to 10 kHz). Real-time measurement of droplet frequency, droplet spacing, effective droplet diameter, droplet count and nominal bulk fluid flow rates are easily detected. FIG. 10, shows a trans-illumination scheme but the invention can also include any illumination scheme, including but not limited to, epi-illumination and dark-field illumination schemes. The invention includes a light source, illumination optics, imaging optics and a linear sensor array. The light source can include any light source, including but not limited to, LED, laser, incandescent light bulb, fiber optic bundle, and OLED. Preferably, the light source is an LED. The illumination optics can include any illumination optics, including but not limited to, fiber optics, GRIN lens, multiple element lens and light shaping diffusers. A preferred embodiment is a single plano-convex lens positioned such that the LED is imaged at infinity. There may be an aperture to control the illuminated field-of-view to illuminate only the area near the micro-fluidic channel. The imaging optics can include any imaging optics, including but not limited to, cylindrical lens, fiber optics, GRIN lens, anamorphic lenses, and multiple element lenses. A preferred embodiment is a cylindrical lens which images a 2D area from the microfluidic device onto a single line of the linear array sensor. There may be an aperture to control optical aberrations and stray light. The linear sensor array can be any linear sensor array. A preferred embodiment is a high speed (>8 MHz) linear array sensor with at least 128 pixels and 5 µm pixel size.

Figure 11:
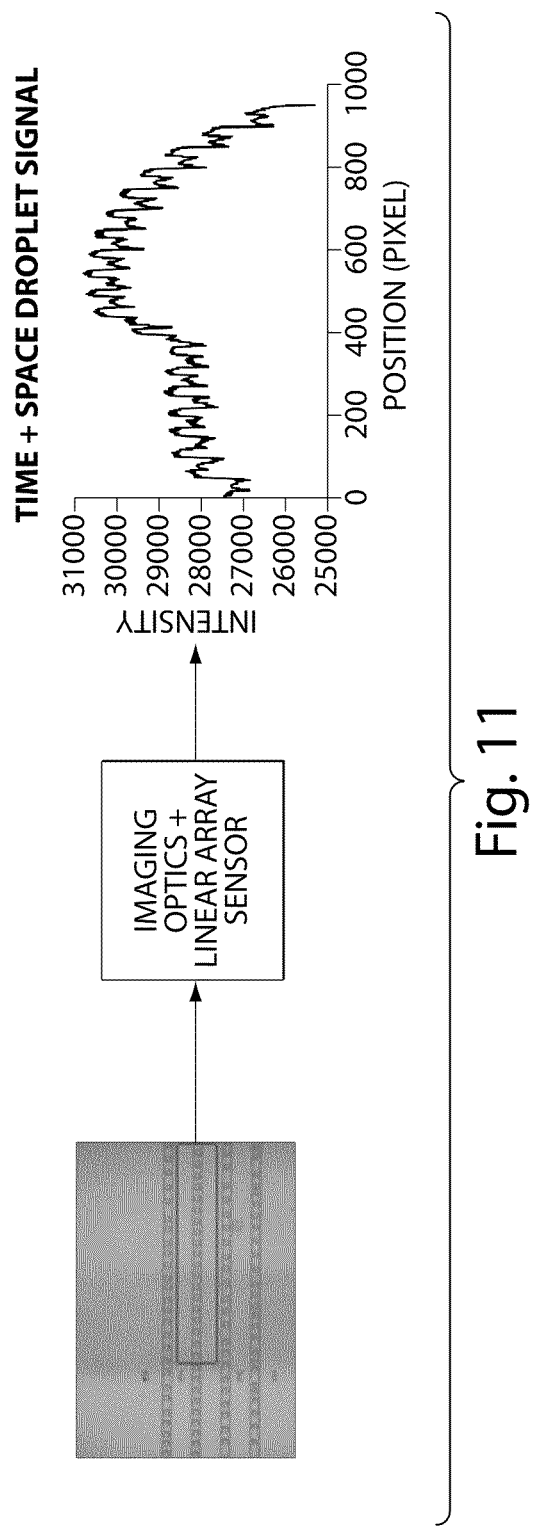
FIG. 11 is a graph showing that the imaging optics "squeezes" a 2D image into a 1D image by optically summing what would be the columns of the blue region of interest into a single line.

In this method, the imaging optics "squeezes" a 2D image into a 1D image by optically summing what would be the columns of the blue region of interest into a single line as shown in FIG. 11. High-speed linear array sensors with 8 MHz and faster readout rates which provide an inexpensive replacement for the area-scan CCD imager are readily available. The high readout rate and linear pixel spacing allows the measurement of droplet parameters with very high precision in time and space respectively.

Figure 12:
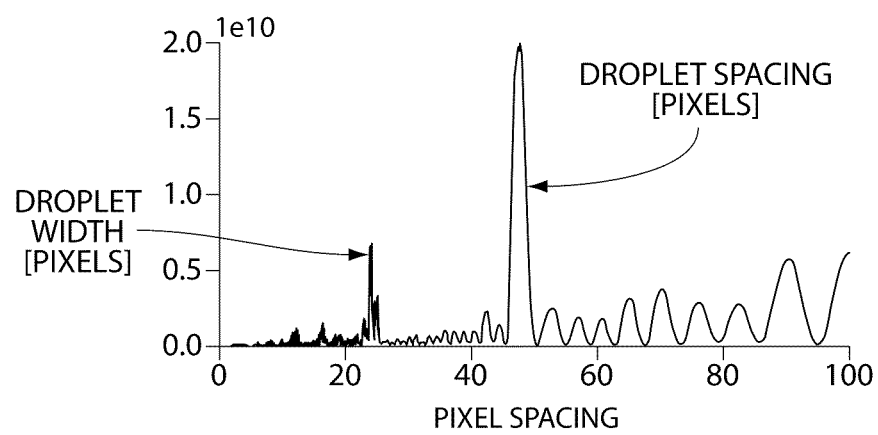
FIG. 12 is a graph showing that the average droplet spacing is approximately 50 pixels and droplet diameter is approximately 25 pixels.

A single image from the linear sensor array allows the measurement of droplet spacing and droplet diameter. As described above and shown in FIG. 11, the output of the linear sensor array clearly shows a periodic signal representing the droplets as they are positioned within the microfluidic channel. Droplet position measured in pixels can be converted to physical position by determining the optical magnification of the imaging optics. There are many ways to analyze period signals but in one embodiment measurement is as follows: (1) compute the Fourier Transform of the 1D image; (2) search for the maximum power signal from the transformed data; (3) the droplet spacing corresponds to the transformed data with maximum power signal. FIG. 12 shows that the average droplet spacing is approximately 50 pixels and droplet diameter is approximately 25 pixels.

Taking many samples over time from the linear sensor array allows the measurement of droplet frequency, droplet count and bulk fluid flow rate. Droplet frequency can be computed by applying the Fourier Transform to the time data in a similar manner to the analysis performed on the spatial data described previously. Typical linear sensor arrays have readout rates at 8 MHz and above, this easily allows the measurement of each droplet at typical droplet generation rates of up to 10 KHz. The droplet count is determined by integrating the droplet frequency with respect to time. The bulk fluid flow rate is the product of the microfluidic channel cross-sectional area, droplet frequency and droplet spacing.

The combination of image processing and feedback control provide other functionality beyond droplet control. The inherent stability and known reference allows for the use of these components to identify and diagnose issues in the system. The system can be tuned to be robust to run-to-run and intra-run changes in fluid environment, pump controls, and microfluidic device variations. The inherent stability present in this system that is not present in an uncontrolled system, can be used to identify system issues or instabilities. Intra- and inter-run patterns can be used to detect fluidic leaks, restrictions, mechanical issues, and input conditions.

Another secondary byproduct of image processing is the examination of droplets by size across periods of time (i.e., an entire run). By creating a histogram of droplets, a new diagnostic tool was made available. Beyond verification of the feedback control operation, these histograms can identify issues in pre-emulsified library, fluidic interference in the chip, and other system issues.

The present invention also provides a Background Subtraction Algorithm. This method provides improvements over the accumulating contour detection method. Specifically, the Background Subtraction Algorithm improves CPU utilization as this method is less computer intensive. It prevents or decreases sensitivity to variations in illumination and focus quality, when measuring a certain parameter of the detected droplet (like size). Moreover, it prevents or decreases noise amplification when measuring a certain parameter of the detected droplet (like size), due to accumulation of contours of the same droplet. Specifically the Background Subtraction Algorithm is fast, produces less measurement noise and with improved optics, it is possible to use single threshold to detect contours.

Specifically, the Background Subtraction Algorithm takes advantages of the fact that droplets always appear to be moving, it calculates image difference of every two consecutive images. If the absolute value of the maximum difference between images is less then Threshold1, then one of the images is selected and saved as a current background image. This is an image of the channel without droplets. Once background image is obtained each new image is also differenced against the current background image and Threshold2 is applied to the difference image. Contours are then obtained from the binary image and filtered using same circularity, size and position filters described for Contour Accumulation Algorithm. Advantage of the subtraction is that it allows to remove image of the droplet channel that can make it harder to detect outer contour of the droplet which is less prone to size variations due to illumination non-uniformity and defocusing.

A microfluidic system of the present invention includes one or more microfluidic channels. The terms microfluidic system, microfluidic device, microsubstrate, substrate, microchip, and chip are used interchangeably herein. The microfluidic system can include at least one inlet channel, at least one main channel and at least one inlet module. The microfluidic system can further include at least one coalescence module, at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. The dimensions of the substrate are those of typical microchips, ranging between about 0.5 cm to about 15 cm per side and about 1 micron to about 1 cm in thickness. The microfluidic and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227, each of which is incorporated by reference in its entirety.

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

A "main channel" is a channel of the device of the invention which permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets.

The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

The fluids described herein are related to the fluids within a microfluidic device and the fluids used to introduce microdroplets or other items into a microfluidic device.

The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e.g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases. The continuous phase fluid within the main channel of the microfluidic device is referred to as the carrier fluid. The continuous phase fluid outside the main channel of the microfluidic device which is used to introduce a sample fluid (either a continuous sample fluid or a discontinuous sample fluid (e.g., pre-made fluidic droplets) into the microfluidic device is referred to as the drive fluid.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof.

The term "emulsion" refers to a preparation of one liquid distributed in small globules (also referred to herein as drops, droplets or NanoReactors) in the body of a second liquid. For example, the discontinuous phase can be an aqueous solution and the continuous phase can a hydrophobic fluid such as an oil. This is termed a water in oil emulsion. Alternatively, the emulsion may be a oil in water emulsion. In that example, the continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 . . . 5, 10, 15, 20, 25, 30, 35, 40, 45, 50 . . . 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; WO 2006/040554; WO 2004/002627; WO 2004/091763; WO 2005/021151; WO 2006/096571; WO 2007/089541; WO 2007/081385 and WO 2008/063227.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle.

Droplets of a sample fluid can be formed within the inlet module on the microfluidic device or droplets (or droplet libraries) can be formed before the sample fluid is introduced to the microfluidic device ("off chip" droplet formation). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The continuous phase fluid (carrier fluid and the drive fluid) can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Pat. No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; WO 2006/040554; WO 2004/002627; WO 2004/091763; WO 2005/021151; WO 2006/096571; WO 2007/089541; WO 2007/081385 and WO 2008/063227; U.S. Pat. No. 6,540,895 and U.S. Patent Application Publication Nos. 20010029983 and 20050226742

The microfluidic device of the present invention may include one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules producing droplets of samples into the main channel. For example, a first inlet module may produce droplets of a first sample into a flow of fluid in the main channel and a second inlet module may produce droplets of a second sample into the flow of fluid in main channel, and so forth. The second inlet module is preferably downstream from the first inlet module (e.g., about 30 nm). The fluids produced into the two or more different inlet modules can comprise the same fluid or the same type of fluid (e.g., different aqueous solutions). For example, droplets of an aqueous solution containing an enzyme are produced into the main channel at the first inlet module and droplets of aqueous solution containing a substrate for the enzyme are produced into the main channel at the second inlet module. Alternatively, the droplets produced at the different inlet modules may be droplets of different fluids which may be compatible or incompatible. For example, the different droplets may be different aqueous solutions, or produced introduced at a first inlet module may be droplets of one fluid (e.g., an aqueous solution) whereas droplets produced at a second inlet module may be another fluid (e.g., alcohol or oil). The terms "produced" or "producing" are meant to describe forming, generating, or creating droplets from a continuous sample source. Moreover, the term producing encompasses introducing pre-formed droplets (e.g., droplets made off chip) into a microfluidic channel in a microfluidic device.

What is claimed is:

1. A method for manipulating microfluidic droplet pairing ratios comprising:
    providing a microfluidic system comprising at least one microfluidic channel;
    providing a first plurality of fluidic droplets within said microfluidic channel at a first frequency;
    providing a second plurality of fluidic droplets within said microfluidic channel at a second frequency, wherein at least one fluidic droplet from said first plurality and at least one fluidic droplet from said second plurality are paired;
    assessing said first frequency and said second frequency using an image sensor; and
    transmitting said assessment of said first and said second frequencies to a feedback controller; wherein said feedback controller adjusts a flow rate of one or more fluids to provide a desired frequency ratio of said first to said second plurality of droplets, thereby manipulating the pairing ratios of said first and second pluralities of fluidic droplets within said microfluidic channel.

2. The method of claim 1, wherein the first plurality of fluidic droplets and the second plurality of fluidic droplets were provided at the same frequency and wherein said feedback controller adjusts a flow rate of one or more fluids to maintain said first and said second frequency at the same frequency.

3. The method of claim 1, wherein the first and second pluralities of fluidic droplets differ in size, color, refractive index, or extinction coefficient.

4. The method of claim 1, wherein the first and second pluralities of fluidic droplets contain a different biological, biochemical, or chemical entity.

5. The method of claim 1, wherein the desired frequency ratio of the first plurality of droplets to the second plurality of droplets is selected from the group consisting of 1:1, 1:2, 1:3, 1:4, 1:5, 1:6, 1:7, 1:8, 1:9, and 1:10.

6. The method of claim 5, wherein the desired frequency ratio of the first plurality of droplets to the second plurality of droplets is 1:1.

7. The method of claim 1, wherein the image sensor is a linear array sensor.

8. The method of claim 1, wherein said first plurality of fluidic droplets have a maximum cross-sectional dimension of less than about 100 microns.

9. The method of claim 1, wherein said second plurality of fluidic droplets have a maximum cross-sectional dimension of less than about 100 microns.

* * * * *